United States Patent [19]
Albin et al.

[11] Patent Number: 5,124,308
[45] Date of Patent: Jun. 23, 1992

[54] MONOSUBSTITUTED DITHIOOXAMIDE COMPOUNDS AND THEIR USE

[76] Inventors: Loren D. Albin, 117 Gresham Ave. N., Oakdale, Minn. 55119; David R. Boston, 405 Fontaine Ct., Woodbury, Minn. 55125; Derek R. Callaby, 6302 Upper 44th St. N., Oakdale, Minn. 55109; Jacqueline M. Furlong, 3741 Grovner Rd. North, Oakdale, Minn. 55128; Robert J. Lokken, 2612 Southlawn Dr., Maplewood, Minn. 55109; Roger A. Mader, 10240 Perkins Ave., Stillwater, Minn. 55082; David B. Olson, 14490 Racine Ave. N., St. Croix, Minn. 55047; Wayne O. Otteson, 7381 Paul Rd., Woodbury, Minn. 55125; Norman P. Sweeny, 45 Pheasant La., North Oaks, Minn. 55110; Daryle H. Busch, R.R. 1, Box 120 TC, Lawrence, Kans. 66044; Nusrallah Jubran, 2060 Wilson Ave., St. Paul, Minn. 55119

[21] Appl. No.: 438,776

[22] Filed: Nov. 17, 1989

[51] Int. Cl.⁵ .................................. B41M 5/132
[52] U.S. Cl. ........................ 503/217; 427/150; 503/201; 503/210; 503/211; 503/212; 503/216; 503/218
[58] Field of Search .................... 427/150–152; 503/200, 210–212, 216–218, 225, 226, 201, 215

[56] References Cited

U.S. PATENT DOCUMENTS

| | | | |
|---|---|---|---|
| 3,111,423 | 11/1963 | Ostlie | 117/36.8 |
| 3,252,910 | 5/1966 | Oberright | 252/42.7 |
| 3,318,675 | 5/1967 | Olin | 71/2.3 |
| 3,437,677 | 4/1969 | Bertsch et al. | 260/429 |
| 3,481,759 | 12/1969 | Ostlie | 117/36.2 |
| 3,516,846 | 6/1970 | Matson | 117/36.2 |
| 3,658,900 | 4/1972 | Alt | 260/551 S |
| 4,111,462 | 9/1978 | Lange et al. | 282/27.5 |
| 4,232,083 | 11/1980 | Buerkley et al. | 428/307 |

FOREIGN PATENT DOCUMENTS

| | | | |
|---|---|---|---|
| 548341 | of 0000 | Canada | 503/217 |
| 2246025 | 3/1974 | Fed. Rep. of Germany | 26/551 S |
| 112435 | 4/1975 | German Democratic Rep. | 260/551 S |
| 808425 | of 0000 | United Kingdom | 503/217 |

OTHER PUBLICATIONS

Pat. Abstracts of Japan, vol. 6, No. 106 (C-108)(984), Jun. 16, 1982, JP-A-57 034161 (Osaka Soda K.K.) Feb. 24, 1982.
Chem. Abstracts, vol. 54, 1960, Abs. No. 22426e,f, Columbus, OH.
O. Wallach, *Ann.*, 262, 324 (1891).
A. Reissert, *Chem. Ber.*, 37, 3708 (1904).
A. Reissert et al., *Chem. Ber.*, 57B, 981 (1924).
R. N. Hurd et al., *J. Am. Chem. Soc.*, 82, 4454 (1960).
A. D. Grabenko et al., *Zhur. Obshch. Khim.*, 30, 1222 (1960).
R. N. Hurd et al., *J. Org. Chem.*, 26, 3980 (1961).
A. D. Grabenko et al., *Zhur. Obshch. Khim.*, 31, 2739 (1961).

(List continued on next page.)

*Primary Examiner*—Bruce H. Hess
*Attorney, Agent, or Firm*—Merchant, Gould, Smith, Edell, Welter & Schmidt

[57] ABSTRACT

This invention concerns monosubstituted dithiooxamides, and a preferred class comprises those wherein the substituent is such that the resulting dithiooxamide derivative is substantially nonvolatile at about room temperature. Preferred materials are those for which when the monosubstituent dithiooxamide is complexed with a transition metal cation, the resulting polymer is substantially a dark, i.e., preferably blue or blue-black color. Carbonless paper constructions involving use of N-(monosubstituted)dithiooxamides to advantage are described.

19 Claims, 1 Drawing Sheet

OTHER PUBLICATIONS

R. N. Hurd, *Review of the Scientific and Patent Literature on Dithiooxamide, its N-Substituted Derivatives and Their Metal Complexes*, Mallinckrodt Chemical Works, St. Louis, MO, 1963.

B. Persson et al., *J. Acta. Chem. Scand.*, 18, 1059 (1964).

B. J. Haske et al., *J. Org. Chem.*, 32, 1579 (1967).

A. D. Grabenko et al., *Zhur. Org. Khim.*, 8, 528 (1972).

G. C. Pellacani et al., *Inorg. Chem. Acta*, 9, 189 (1974).

R. A. Dommisse et al., *Bull. Soc. Chim. Belg.*, 88, 109 (1979).

F. W. Billmeyer, Jr., and M. Saltzman, *Principles of Color Technology*, John Wiley and Sons; New York, N.Y.; Ch. 2 and 3, 1981.

H. Hofmans et al., *Inorg. Chim. Acta*, 54, L227 (1981).

H. U. Kibbel et al., *J. Prakt. Chem.*, 323, 41 (1981).

H. Hofmans et al., *Spectrochim. Acta*, 38A, 1213 (1982).

H. C. Hofmans et al., *Trans. Met. Chem.*, 9, 213 (1984).

H. Hofmans et al., *Bull. Soc. Chim. Belg.*, 94, 705 (1985).

H. Hofmans et al., *Bull. Soc. Chim. Belg.*, 95, 83 (1986).

M. R. Green et al., *Inorg. Chem.*, 26, 2326 (1987).

*Chem. Abstr.*, 68, 39331 (1968).

MONOSUBSTITUTED DITHIOOXAMIDE COMPOUNDS AND THEIR USE

FIELD OF THE INVENTION

The present invention relates to N-(monosubstituted)dithiooxamides and to their reactions with metal salts to form coordination compounds. The invention also concerns the use of such materials in the preferred generation of a dark image upon polymer formation, for example during the application of appropriate pressure to pressure sensitive imaging constructions such as carbonless paper constructions.

BACKGROUND OF THE INVENTION

The present invention generally concerns dithiooxamide (rubeanic acid) and substituted dithiooxamide compounds. Dithiooxamides are compounds of the general formula I, as follows:

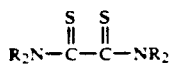

wherein: typically each R is independently H, an alkyl group, or a substituted alkyl group, although other substituents as outlined herein below, on each N atom are possible. When it is said that each R is "independently" one of the named substituents, it is meant that there is no requirement that all groups R be the same.

The "non-N-substituted" member of the family of compounds designated by formula I, i.e., wherein all groups "R" are "H", is generally referred to herein as "dithiooxamide" or by its formula $H_2NC(S)C(S)NH_2$. Dithiooxamide is a well-known and widely studied compound. Because it presents four potential sites for coordination (two sulfur atoms and two nitrogen atoms) certain dithiooxamides according to formula I above are good agents for forming coordination compounds with transition metal salts. In particular, certain compounds according to the general formula I have been shown to form coordination complexes with transition metal cations; for example, cations of nickel, zinc, palladium, platinum, copper, iron, and cobalt.

At least because of its relatively high vapor pressure and water solubility, unsubstituted dithiooxamide, i.e., formula I wherein each "R" group is "H", is an inconvenient reagent for use in forming complexes with transition metals under certain circumstances, as for example in pressure sensitive imaging constructions. Also, because of the instability of unsubstituted dithiooxamide in the encapsulation process involved in the manufacture of pressure sensitive imaging constructions, i.e., impact imaging constructions or image transfer constructions, it is an inconvenient reagent for such an application.

In part to avoid such problems, N-substituted analogs have been formed and studied. Some of the better known of these are the N,N'-(disubstituted)dithiooxamide compounds, i.e., compounds according to the general formula II, as follows:

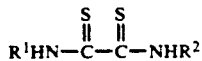

wherein: $R^1$ and $R^2$ are independently selected from the group generally comprising alkyl groups, substituted alkyl groups, aryl groups, and substituted aryl groups; the above-listed groups including within their scope groups containing heteroatoms, and cycloaliphatic structures. The better known such compounds are symmetrically substituted compounds, i.e., compounds wherein $R^1$ and $R^2$ are the same.

Because dithiooxamides possess four possible sites for coordination, they can theoretically form at least three general types of coordination modes with a transition metal "M", as is represented by the following formulae III, IV, and V.

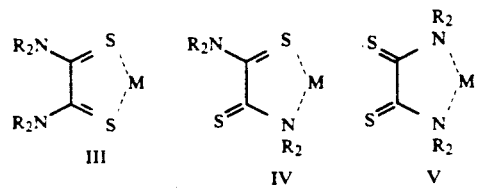

It will be understood that if the dithiooxamide involved in coordination is asymmetric, i.e., is substituted differently at the two nitrogen atoms, then there would be two possible types of coordination represented by formula IV.

Also, when the uncomplexed dithiooxamides have at least two amide protons, with at least one H-atom on each N-atom in the molecules as represented by formulae I or II, at least three general types of coordination compounds or complexes are possible, as is represented by formulae VI, VII, and VIII.

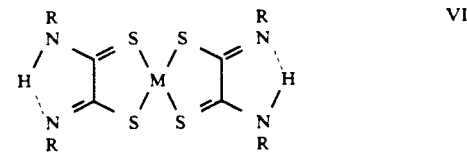

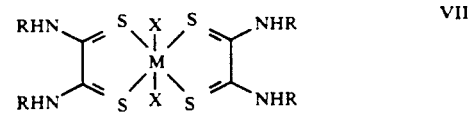

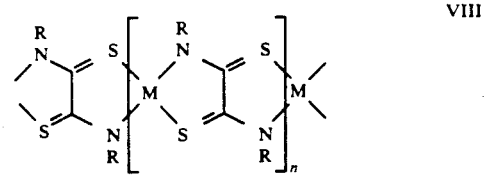

Herein, continued reference will be made to the three different general types of transition metal complexes of dithiooxamides represented by VI, VII, and VIII. The first of these (formula VI) will be generally referred to herein as a "monomer" complex and comprises a coordination complex of two equivalents dithiooxamide per equivalent of transition metal. The second type (formula VII) will be referred to as a "cationic" complex, and the third type (formula VIII) will be referred to as a "polymer".

In the coordination compound generally referred to herein as the "monomer" or "monomer complex" (formula VI), the transition metal generally has an oxidation state of +2, and each equivalent of dithiooxamide has an overall charge of −1, as a result of the removal of one amide proton. This coordination compound will generally be referred to herein as a 2:1 adduct of ligand to metal atom, or according to the formula $M(HL)_2$ typically wherein: $M=Ni^{+2}$, $Zn^{+2}$, $Cu^{+2}$, $Co^{+2}$, $Fe^{+2}$, $Cd^{+2}$, $Hg^{+2}$, $Pb^{+2}$, $Pd^{+2}$, or $Pt^{+2}$; and, HL refers generally to the "ligand", i.e., unsubstituted or substituted dithiooxamide having a charge of $-1$, due to removal of a thioamide proton.

Generally, in the representation of the "monomer" (formula VI) the coordinating sulfur atoms are in the same plane. It will be understood that alternative isomers to formula VI are possible. For example, the functional groups could be oriented such that each ligand is coordinated through a nitrogen atom and a sulfur atom to the metal center.

Certain monomer complexes containing N,N'-(disubstituted)dithiooxamides have been described in the literature. For example, in R. A. Dommisse et al., *Bull. Soc. Chim. Belg.* 1979, 88, 109, bis(N,N'-diisobutyldithiooxamide)Pd(II) and bis(N,N'-diisobutyldithiooxamide)Pt(II) were described; and in H. Hofmans et al., *Bull. Soc. Chim. Belg.* 1985, 94, 705, the authors reported the crystal structure of bis(N,N'-dicyclopropyldithiooxamide)Pd(II). In general, formation of a monomer complex requires maintaining a ratio between the ligand and the cation of at least two to one in neutral media.

The second type of coordinating complex involving dithiooxamide is referred to herein as a "cationic" complex. The coordination is generally represented by formula VII above and comprises a complex wherein: the transition metal cation has an oxidation state of $+2$; the dithiooxamide ligand is neutral; there are two dithiooxamide ligands per equivalent of metal cation; and, there are two anions (for example, halogen anions) associated with the complex. It will be understood that formula VII is merely a representation of the stoichiometry of the cationic complex, and does not necessarily require that the ligands labeled "X" be coordinated trans to each other or that they be directly coordinated to the metal. Also, while coordination of the ligand is shown as involving sulfur atoms only, alternative coordination may be possible.

Herein, the cationic complex is referred to by the general formula $M(H_2L)_2X_2$ wherein: M is a transition metal cation having a valence of $+2$, for example, $Ni^{+2}$, $Zn^{+2}$, $Pd^{+2}$, $Pt^{+2}$, $Cu^{+2}$, $Fe^{+2}$, $Cd^{+2}$, $Hg^{+2}$, $Pb^{+2}$, or $Co^{+2}$; $H_2L$ is a dithiooxamide ligand having two amide hydrogens therein, with one H-atom on each amide nitrogen; and, X is an anion having a charge of $-1$, for example, $Br^-$, $Cl^-$, $F^-$, or $I^-$. Cationic complexes have been described in, for example, M. R. Green et al., *Inorg. Chem.* 1987, 26, 2326 and G. C. Pellacani et al., *Inorg. Chim. Acta* 1974, 9, 189.

The third complex of interest herein is referred to as a "polymer" complex, and generally comprises a complex with about a 1:1 ratio of ligand to transition metal cation. The actual ratio of ligand to metal is typically, however, a little greater than 1:1, since the "polymer" complex may comprise low molecular weight oligomers, and therefore generally includes more ligands, since they are end groups, than metal cations. The ligand has an overall charge of $-2$ due to removal of two amide protons, i.e., one from each amide group, and the transition metal cation has an oxidation state of $+2$. One theoretical structural formula for such a polymer complex is generally represented above by formula VIII.

It will be understood that alternative coordination is possible and that the structure shown in formula VIII merely represents the general stoichiometry, and one possible structure, of the polymer. That is, the polymer need not necessarily possess the symmetry shown in formula VIII. For example, the polymer would still be possible in isomeric structures wherein each dithiooxamide ligand does not necessarily have one nitrogen and one sulfur coordinated with each associated metal cation.

The polymer complex will be generally referred to herein as such, or according to the general formula $(ML)_n$ wherein: M is a transition metal cation having an oxidation state of $+2$, for example $Ni^{+2}$, $Zn^{+2}$, $Pd^{+2}$, $Pt^{+2}$, $Cu^{+2}$, $Fe^{+2}$, $Cd^{+2}$, $Hg^{+2}$, $Pb^{+2}$, or $Co^{+2}$; and, L is a dithiooxamide ligand having a charge of $-2$, i.e., a dithiooxamide or substituted dithiooxamide molecule having one amide hydrogen removed from each of the amide groups. The designation "n" is merely an integer, indicating polymer structure.

Some polymer complexes involving substituted dithiooxamides are known. In general, the known complexes often involve symmetrically disubstituted dithiooxamides according to the general formula II above. Such polymer complexes are frequently characterized by their exhibition of a deep color. In particular the $Ni^{+2}$ polymer complex of symmetrically disubstituted dithiooxamides (where the groups $R^1$ and $R^2$ in formula II are aliphatic) are often magenta, purple, or red. Examples of polymer complexes containing substituted dithiooxamide ligands are disclosed in R. N. Hurd et al., *J. Am. Chem. Soc.* 1960, 82, 4454; H. Hofmans et al., *Spectrochim. Acta* 1982, 38A, 1213; and R. N. Hurd, *Review of the Scientific and Patent Literature on Dithiooxamide, its N-Substituted Derivatives and Their Metal Complexes*, Mallinckrodt Chemical Works, St. Louis, Mo., 1963.

The chemistry and characteristics of dithiooxamide compounds have been exploited commercially. For example, dithiooxamide compounds, with transition metal cations having a $+2$ valence state, have been used in the preparation of carbonless image transfer products or constructions. Carbonless imaging constructions, or products employing this chemistry, generally involve placement of one reactant (i.e., one of the transition metal or ligand material) on one substrate (for example, sheet of paper) and the other reactant (the one of transition metal or ligand material not used on the first substrate) on a second, i.e., mating, substrate. The ligand material and metal are maintained separated from contact and reaction with one another. This is typically accomplished by encapsulation of one of the reactants. Herein, the terms "encapsulation" and "encapsulated compounds" refer to microcapsules enclosing a fill material therewithin.

Once rupturing pressure is applied to the construction, as from a stylus or business-machine key, the encapsulated reactant is released, and a complex between the previously separated reactants is formed. In general, the resulting complex will, of course, form a colored image corresponding to the path traveled by the stylus, or the pattern of pressure provided by the key.

In one commercial product, the capsules on a first sheet (donor sheet) contain dithiooxamide (DTO) derivatives, and the mating sheet, sometimes referred to as the receptor sheet, contains a coating of selected salts of nickel. The encapsulated dithiooxamide compounds, in a suitable binder, are coated onto one face of the donor sheet; and, the metal salt, optionally in a suitable binder, is coated onto one face of the receptor sheet. Herein, the term "suitable binder" refers to a material, such as starch or latex, that allows for dispersion of the reactants in a coating on a substrate, and is readily rupturable under hand-held stylus pressure, or typical business machine key pressure. When the two coated faces are contacted such that the dithiooxamide compound and the metal salt can combine and react, a coordination complex forms and an image results. Typically, this occurs by transfer of the ligand material to the site of the metal salt, i.e., transfer of the ligand material from the donor sheet to the receptor sheet. The image, of course, forms on the receptor sheet.

In a preferred orientation, the encapsulated ligand material, in a suitable binder, is coated on the back of the donor sheet, sometimes referred to as a coated back (CB) sheet, and the metal salt, optionally in a suitable binder, is coated on the front of the receptor sheet, or coated front (CF) sheet. Again, in imaging, the two sheets are positioned such that the encapsulated ligand material on the donor (CB) sheet faces the metal salt coating on the receptor (CF) sheet. When pressure is applied to the uncoated surface of the donor sheet, i.e., the face nor in contact with the receptor (CF) sheet, selected capsules rupture (i.e., those capsules corresponding to the pattern of applied pressure) with release of the ligand material for transfer to the receptor sheet, forming a colored pattern due to complexing with the salt. In many applications the uncoated surface of the donor (CB) sheet comprises a form of some type. The stylus pressure is generated by means of a pen or other writing instrument used in filling out the form. Thus, the image appearing on the receptor (CF) sheet is a copy of the image applied to the top sheet.

In some applications, multiple form sets have been used. These contain intermediate sheets having a metal salt coating on one side and a coating with capsules of ligand material on the opposite side. Such sheets are generally referred to herein as "CFB" sheets (i.e., coated front and back sheets).

Due to the stoichiometry of the system (i.e., the metal salt is usually in excess since relatively little of the encapsulated ligand material is released), it is generally believed that the image formed on the receptor sheet, after stylus pressure is applied to break the capsules and release the encapsulated compound, results from the polymer complex. That is, the color generally results from $(ML)_n$ material, but is not necessarily limited to that. The monomer complex, $M(HL)_2$, may also be present in small amounts, or as an intermediate in the formation of the polymer. The anion of the transition metal salt, which is usually the conjugate base of a weak acid, may facilitate removal of the two amide protons from the substituted dithiooxamide compounds, necessary for polymer complexation with the $M^{+2}$ cation.

Certain dithiooxamide materials have been utilized in commercially available carbonless paper products. Generally, they comprise symmetrically disubstituted dithiooxamide compounds and include N,N'-dibenzyldithiooxamide and N,N'-di(2-octanoyloxyethyl)dithiooxamide.

In commercial applications, generally, nickel salts have been preferred as the transition metal salts. One reason for this is that nickel salts form a deep color when complexed with the dithiooxamide ligands. The nickel salts are also substantially colorless, and thus do not alone impart color to the receptor (CF) sheet. A third reason is that nickel salts are relatively low in cost, by comparison to other transition metal salts that can be easily and safely handled and that form highly colored coordination complexes with dithiooxamides.

It is desirable that the color of the complex be a deep, strong color that is not only pleasing to the eye, but that will exhibit good contrast with the paper, for purposes of later reading and/or photocopying. This has been one drawback with conventional carbonless paper arrangements, which use nickel salts complexed with disubstituted dithiooxamide ligands. The image imparted by the resulting coordination compound, under such circumstances, is generally magenta. The more "red" character the polymer complex exhibits, generally, the less contrasting and pleasing is the appearance. A dark, i.e., preferably black, blue, or blue-black, arrangement would be preferred, but previously such has not been satisfactorily obtainable.

In conventional impact imaging constructions, the capsules can be inadvertently ruptured in steps such as processing, printing, cutting, packaging, handling, storing, and copying. In these situations inadvertant marking or discoloration (i.e., backgrounding) of the sheets results due to inadvertant capsule rupture and transfer of the encapsulated material to the mating sheet where color formation occurs. The amount of inadvertant backgrounding has been reduced in such products by the use of a color control coreactant distributed externally among the capsules. This coreactant is capable of reacting with the contents of the ruptured capsules before transfer of said contents to the receptor sheet and formation of an undesired image. See D. A. Ostlie, U.S. Pat. No. 3,481,759 (1969).

The dithiooxamide compounds generally useful in carbonless paper constructions should be relatively nonvolatile, so that free dithiooxamide compounds, which would result from any inadvertently ruptured capsule, does not readily transfer from the donor sheet to the receptor sheet and form undesired spots of imaged area. That is, so that without the specific assistance of stylus or key pressure, transfer is not readily obtained. Also, preferably the encapsulated ligand material should be colorless, since the ligand material is often encapsulated and coated on the backside of a sheet, such as a form, which has printing on one or both sides thereof. This aspect is particularly important if the donor sheet comprises a top sheet for a stack of carbonless papers. Such sheets are often white, so that they can be readily identified as originals, can be readily photocopied, and can be easily read.

It is also desirable that the ligand material be capable of being encapsulated and of rapidly forming a stable colored image upon contact with the metal cation on the receptor sheet. That is, the transition metal complex should form nearly instantaneously, so that the image is rapidly formed as the stylus pressure is applied to the backside of the donor sheet. This will help ensure formation of an accurate, almost instantly readable, copy. The image should also be relatively stable so that it does not substantially fade with time.

While the above-described preferred characteristics have long been desirable, they have not been satisfactorily achieved with conventional reactants and conventional constructions. What has been needed has been suitable materials and arrangements for achieving the desired features described.

SUMMARY OF THE INVENTION

In part, certain embodiments of the present invention developed from the observation that certain N-(monosubstituted)dithiooxamides are colorless and form darkly colored images on coordination with certain transition metal ions such as nickel. When such dithiooxamides are employed in applications such as image transfer constructions, i.e., carbonless paper, a more pleasing and more highly contrasting image is thus formed. Preferred compounds described herein form a dark image, i.e., preferably a blue or blue-black color.

Monosubstituted dithiooxamides according to certain preferred embodiments of the present invention are generally represented by formula IX as follows:

$$H_2N-\overset{\overset{\displaystyle S}{\|}}{C}-\overset{\overset{\displaystyle S}{\|}}{C}-NHR' \qquad IX$$

wherein: R' is a suitable substituent such that: the resulting dithiooxamide derivative is substantially nonvolatile at about room temperature, i.e., surpasses the volatility test stated herein below for use in applications in which premature imaging (backgrounding) is a potential problem, as for example in carbonless paper constructions; and, the resulting dithiooxamide is substantially colorless. Preferably, R' is a substituent that is sufficient to render a substantially dark, i.e., blue or blue-black, color upon coordination of the resulting dithiooxamide to a transition metal cation having a +2 oxidation state, such as, for example, $Ni^{+2}$.

A variety of substituents may comprise R'. In general, R' includes within its scope alkyl and aralkyl groups as defined below. The alkyl and aralkyl groups may be functionalized by a variety of substituents. Aromatic groups are generally excluded from formula IX because the resulting compounds are generally not colorless.

By the above-listed requirement, it is not meant that the resulting preferred dithiooxamides must render a blue or blue-black polymer complex with all transition metal cations having a +2 oxidation state. Rather, a blue or blue-black complex should form with at least one transition metal cation having a +2 oxidation state, thereby enabling preferred utilization of the N-(monosubstituted)dithiooxamide compound for applications wherein a dark polymer complex is desired.

Preferably, and more specifically, it has been determined that the above requirements (relating to colorless ligand, color of polymer, and volatility) are generally met if R' in formula IX is $R^3$; wherein $R^3$ is:

(a) an alkyl or aralkyl group having 11 or more carbon atoms, preferably having 14 or more carbon atoms, and most preferably having 18 or more carbon atoms; or (b) a group of the structure $-R^4-Y-R^5$ wherein:
  (i) when Y is a functional group selected from the group including $-N(R^6)C(O)-$, $-C(O)N(R^6)-$, $-N(R^6)C(O)O-$, $-OC(O)N(R^6)-$, $-N(R^6)C(O)N(R^7)-$, wherein $R^6$ and $R^7$ are independently hydrogen, an alkyl or aralkyl group having 1 to 12 carbon atoms: (A) $R^4$ is a divalent alkyl or divalent aralkyl group having 1 to 12 carbon atoms; (B) $R^5$ is hydrogen, an alkyl or aralkyl group having 1 to 20 carbon atoms, preferably having 2 to 10 carbon atoms; and, (C) the total number of carbons in $R^4$ plus $R^5$ is at least 7; or
  (ii) when Y is a functional group selected from the group including $-OC(O)-$, $-C(O)O-$, $-OC(O)O-$: (A) $R^4$ is a divalent alkyl or divalent aralkyl group having 1 to 12 carbon atoms; (B) $R^5$ is hydrogen, an alkyl or aralkyl group having 1 to 20 carbon atoms, preferably having 3 to 11 carbon atoms; and, (C) the total number of carbons in $R^4$ plus $R^5$ is at least 9.

In the above-listed requirements for R', $R^3$, and herein, the terms "alkyl group" and "divalent alkyl group" include straight chain, branched, cyclic, saturated, and unsaturated (alkylene and alkylyne) groups, and include such when functionalized, for example, by heteroatom substitution on the alkyl groups. Such functional groups include, but are not limited to, hydroxyl, halide, amine, and thiol groups. Herein, "divalent alkyl group" refers to a group resulting from the removal of two hydrogen atoms from one or more carbon atoms of a hydrocarbon. Herein, "aralkyl group" refers to a radical in which an aryl group is substituted for a hydrogen atom of an alkyl group. The term "aralkyl group" does not include, however, aryl groups that would be directly bonded to the nitrogen of the dithiooxamide structure, i.e., where the amido nitrogen of the dithiooxamide structure is substituted directly onto the aromatic ring. Herein, this type of substituent is referred to as an "aromatic group" or substituent. Furthermore, the term "nonaromatic group" refers to any group within the broad definition of R' other than an "aromatic group" as defined.

Classes or families of compounds that meet the above-listed requirements include monosubstituted dithiooxamides in which the substituent, $R^3$, is a long chain alkyl group, or contains a carboxyl group, preferably as an ester, amide, carbonate, carbamide, or carbamate functionality. Compounds within the scope of the above-listed definitions include, for example, N-(6-butanoylamidohexyl)dithiooxamide; N-(2-octanoyloxyethyl)dithiooxamide; N-dodecyldithiooxamide; N-(11-carboxydecyl)dithiooxamide; and, N-(1-naphthylmethyl)dithiooxamide.

From the above, it will be understood that a wide variety of groups are to be understood as included within the general definition of the group R' in formula IX recited above. Three general types of groups, however, are to be understood as specifically excluded when R' is defined as $R^3$. That is, the limitations on $R^3$ exclude these general types of groups. These are:

(a) aromatic groups where the amido nitrogen of the dithiooxamide structure is substituted directly onto the aromatic ring;

(b) groups wherein $R^3$ is sufficiently small and/or sufficiently polar to render the dithiooxamide water soluble and thus nonencapsulatable; and (groups wherein the resulting dithiooxamide would be sufficiently volatile, at about room temperature, to be undesirable in applications such as carbonless paper constructions.

It is apparent from the previous discussion at least some of the reasons why the groups according to paragraphs (b) and (c) are excluded from IX, wherein R' is $R^3$. Compounds, as defined by paragraph (a) are excluded from these preferred compounds, but not necessarily from all aspects of the inventions, at least because the aromatic derivatives are colored in the uncomplexed state and would impart color to the coated back sheet.

Preferred classes of compounds according to the invention for use in carbonless paper constructions include monosubstituted dithiooxamides in which the substituent, $R^3$: is a long-chain alkyl or aralkyl group, e.g., $H_2NC(S)C(S)NHR^3$, wherein $R^3$ is an alkyl or aralkyl group of at least 14 carbons; contains an ester linkage, e.g., $H_2NC(S)C(S)NHR^4OC(O)R^5$, wherein R⁴ and R⁵ are as described above; or, contains an amide linkage, e.g., H₂NC(S)C(S)NHR⁴N(R⁶)C(O)R⁵, wherein R⁴, R⁵, and R⁶ are as described above.

Note that the definitions for R⁴ and R⁵ are generally derived from the data in the tables listed herein below, which define substituents that produce nonvolatile monosubstituted dithiooxamide derivatives. For example, for N-(2-octanoylamidoethyl)dithiooxamide, the number of carbons in R⁴ is 2 and the number of carbons in R⁵ is 7; i.e., the total number of carbon atoms in R⁴ plus R⁵ is 9. The dithiooxamide compound containing the 2-octanoylamidoethyl substituent was observed to be nonvolatile. Generally, it is noted that the ester derivatives are more volatile than the analogous derivatives containing an amide linkage, especially at elevated temperatures. Therefore, there is a distinction between the statement of the acceptable and claimed sum of the number of carbons in R⁴ plus R⁵ for amide substituents and for ester substituents.

Examples of preferred monosubstituted dithiooxamides included within the scope of the present invention, generally represented by formula IX, include:
N-tetradecyldithiooxamide
N-hexadecyldithiooxamide
N-octadecyldithiooxamide
N-(2-octanoyloxyerhyl)dithiooxamide
N-(2-decanoyloxyethyl)dithiooxamide
N-(2-dodecanoyloxyethyl)dithiooxamide
N-(2-hexanoylamidoethyl)dithiooxamide
N-(2-octanoylamidoethyl)dithiooxamide
N-(6-propanoylan:idohexyl)dithiooxamide
N-(6-butanoylamidohexyl)dithiooxamide In general, the above-identified representative compounds satisfy the requirements of solubility in suitable solvents for encapsulation, nonsolubility in aqueous media, and low volatility at room temperature, i.e., about 25° C. In addition, they are generally colorless to lightly colored compounds, and impart little or no color to the sheets upon which they are coated in use. Finally, they form generally blue or blue-black colors on coordination with at least some transition metal ions, such as nickel.

The most preferred compounds satisfy all the above requirements, plus they are generally nonvolatile at elevated temperatures, i.e., above about 25° C., most preferably above about 49° C. The most preferred compounds include: monosubstituted dithiooxamides with either long-chain alkyl or aralkyl groups containing 18 or more carbons, as for example N-octadecyldithiooxamide; and substituents containing an amide functionality according to the formula R⁴—Y—R⁵ defined above wherein Y is —N(R⁶)C(O)—, and the sum of the number of carbons in R⁴ plus R⁵ is at least 8. That these materials are the most preferred will be apparent from the experiments as reported herein below.

The present invention also includes within its scope certain complexes formed from compounds according to formula IX, including polymer complexes. Thus, the present invention encompasses within its scope polymers with the general formula $(ML)_n$ wherein M is a transition metal cation having an oxidation state of +2, preferably a cation selected from the group consisting of $Ni^{+2}$, $Zn^{+2}$, $Pd^{+2}$, $Pt^{+2}$, $Cu^{+2}$, $Fe^{+2}$, $Cd^{+2}$, $Hg^{+2}$, $Pb^{+2}$, and $Co^{+2}$; and, L is a dithiooxamide ligand according to the general formula IX wherein two amide hydrogens have been removed, one from each amide group, rendering an overall charge of −2, as in the following representation.

$$\left[ \begin{array}{c} S \quad S \\ \parallel \quad \parallel \\ HN-C-C-NR' \end{array} \right]^{-2}$$

The invention further includes within its scope the provision of a carbonless transfer system or construction utilizing an N-(monosubstituted)dithiooxamide compound as a reactant. In a preferred embodiment, the construction comprises: a receptor sheet having a coating of transition metal salt, preferably a $Ni^{+2}$ salt, thereon; and, a donor sheet having encapsulated compound according to the following formula thereon:

$$\begin{array}{c} S \quad S \\ \parallel \quad \parallel \\ H_2N-C-C-NHR^8 \end{array}$$

wherein R⁸ is a suitable substituent such that the dithiooxamide compound is substantially nonvolatile at about 25° C. The encapsulation provides means inhibiting reaction between the dithiooxamide compound and the transition metal cation, until appropriate activating pressure is applied to the arrangement.

It will be understood that in some instances the encapsulated material may comprise a mixture of monosubstituted dithiooxamide (capable of forming blue or blue-black image on coordination) and disubstituted dithiooxamide (capable of forming magenta or purple color). Should this latter be the case, a generally dark overall color would result upon image formation, provided, however, that an effective amount (i.e., an amount effective to produce a dark blue or blue-black image rather than a magenta or purple image) of N-(monosubstituted)dithiooxamide were present. Generally, in such mixtures, at least about 40 wt-% of the monosubstituted dithiooxamide is present, for achievement of a dark image.

The invention also includes within its scope a method of forming an image. A preferred embodiment of this method comprises providing a receptor sheet having a surface with a transition metal salt coated thereon; and, transferring to the coated surface of the receptor sheet an effective amount of an N-(monosubstituted)dithiooxamide compound. The N-(monosubstituted)dithiooxamide compound can be volatile or nonvolatile; however, in preferred applications, it will be a nonvolatile compound according to formula IX. Most preferably, the group comprising the substituent on the dithiooxamide nitrogen will comprise a group according to R³ as defined above.

Finally, the present invention includes within its scope methods involving the use of the polymer complex as above-described, and/or monosubstituted dithiooxamides, preferably monosubstituted dithiooxamides according to formula IX.

DETAILED DESCRIPTION OF THE INVENTION

Figure 1:
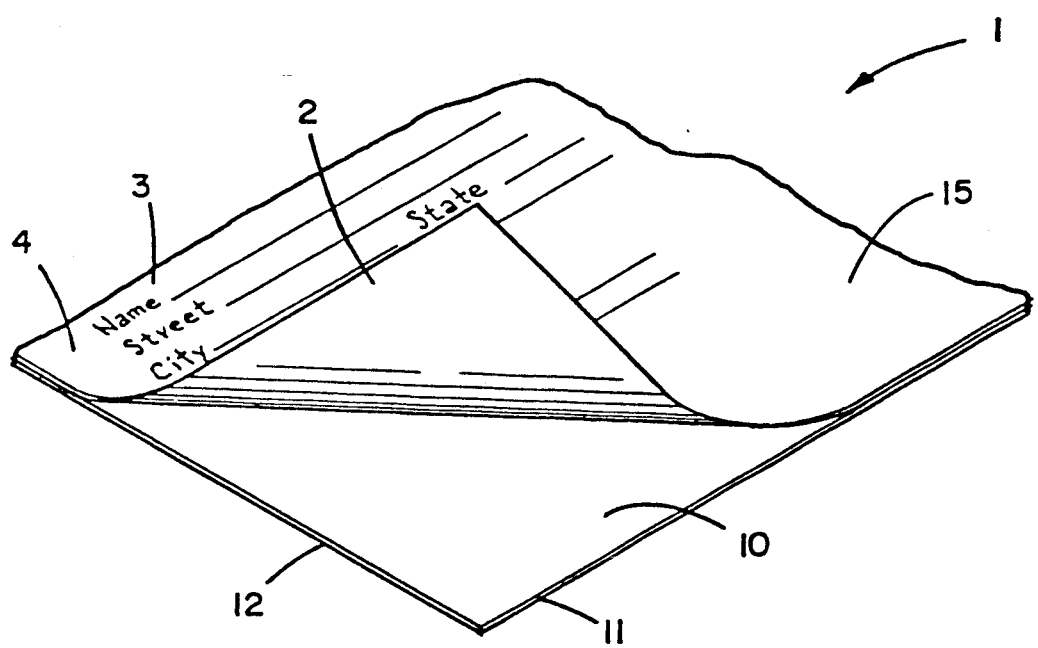
FIG. 1 is a fragmentary perspective view of a carbonless paper construction according to the present invention, depicted with first and second substrates thereof partially separated.

As required, detailed descriptions of the present invention are provided herein. In general, the detailed descriptions are to be considered as exemplary only.

Therefore, the invention is not to be interpreted as limited except as defined by the claims.

N-(Monosubstituted)dithiooxamides

The present invention includes within its scope a novel class of N-(monosubstituted)dithiooxamides according to the general formula:

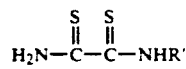
$$H_2N-\underset{\|}{\overset{S}{C}}-\underset{\|}{\overset{S}{C}}-NHR' \qquad IX$$

wherein: R' is a suitable substituent such that the resulting dithiooxamide derivative is substantially nonvolatile at about 25° C., i.e., surpasses the volatility test stated herein below for use in applications involving image formation, as for example a carbonless paper construction; and, R' is such that the resulting dithiooxamide is substantially colorless. Preferably, R' is a substituent that is sufficient to render a substantially blue or blue-black color when the resulting dithiooxamide is used to form a polymer complex with a transition metal cation that has an oxidation state of $+2$, such as $Ni^{+2}$, $Zn^{+2}$, $Pd^{+2}$, $Pt^{+2}$, $Cu^{+2}$, $Fe^{+2}$, $Cd^{+2}$, $Hg^{+2}$, $Pb^{+2}$, or $Co^{+2}$. Herein, R' is defined as any alkyl or aralkyl group, which may be functionalized by a variety of substrates.

As stated previously, this above-listed requirement for preferred compounds does not mean that the resulting dithiooxamide must render a blue or blue-black polymer complex with all transition metal cations having an oxidation state of $+2$. At least one transition metal, however, should form a dark blue or blue-black coordination complex with the preferred N-(monosubstituted)dithiooxamide ligands. In this manner, the N-(monosubstituted)dithiooxamide compound is rendered useable for applications wherein a dark polymer complex, for example, for high contrast, is desired.

Preferably, and more specifically, it has been determined that the above preferred characteristics (colorless uncomplexed ligand material; nonvolatile; and, dark blue or blue-black complex) are generally met if R' is more specifically defined as $R^3$; and $R^3$ is:

(a) an alkyl or aralkyl group having 11 or more carbon atoms, preferably having 14 or more carbon atoms, and most preferably having 18 or more carbon atoms; or (b) a group of the structure $-R^4-Y-R^5$ wherein:

(i) when Y is a functional group selected from the group including $-N(R^6)C(O)-$, $-C(O)N(R^6)-$, $-N(R^6)C(O)O-$, $-OC(O)N(R^6)-$, $-N(R^6)C(O)N(R^7)-$, wherein $R^6$ and $R^7$ are independently hydrogen, an alkyl or aralkyl group having 1 to 12 carbon atoms: (A) $R^4$ is a divalent alkyl or divalent aralkyl group having 1 to 12 carbon atoms; (B) $R^5$ is hydrogen, an alkyl or aralkyl group having 1 to 20 carbon atoms, preferably having 2 to 10 carbon atoms; and, (C) the total number of carbons in $R^{4\ plus\ R5}$ is at least 7; or (ii) when Y is a functional group selected from the group including $-OC(O)-$, $-C(O)O-$, and $-OC(O)O-$: (A) $R^4$ is a divalent alkyl or divalent aralkyl group having 1 to 12 carbon atoms; (B) $R^5$ is hydrogen, an alkyl or aralkyl group having 1 to 20 carbon atoms, preferably having 3 to 11 carbon atoms; and, (C) the total number of carbons in $R^4$ plus $R^5$ is at least 9.

As stated herein, the terms "alkyl group" and "divalent alkyl group" include hydrocarbon groups consisting of straight chains, branched chains, cyclic structures (cycloalkyl and cycloalkylene), saturated groups, unsaturated groups (alkylene and alkylyne); and, the terms include compounds having functional groups. The term "functional group" (and variants thereof) refers to groups including heteroatoms substituted onto the "alkyl group". Such functional groups include within their scope hydroxyl, halide, amine, and thiol groups. It is noted that when "amine" is used, NHR, $NH_2$, and $NR_2$, are included. It is also noted that "divalent alkyl group" generally refers to a group resulting from the removal of two hydrogens from one or more carbons of the group. Herein, "aralkyl group" refers to a radical in which an aryl group is substituted for a hydrogen atom of an alkyl group. The term "aralkyl group" does not include, however, substituents herein referred to as an "aromatic group." The distinction is such that an "aromatic group" is one in which the aromatic ring is directly bonded to an amido nitrogen of the dithiooxamide structure. Thus, the term "aralkyl group" includes within its scope aromatic rings within the main chain of the alkyl group, and/or pendant therefrom, but not directly bonded to the nitrogen atom of dithiooxamide. Note that all groups other than "aromatic groups" as defined herein fall within the definition of "nonaromatic groups." This includes alkyl and aralkyl groups as defined above.

In the above-listed requirements for $R^3$, the Y groups listed represent carbonyl-containing groups, i.e., ester, amide, carbamide, and carbamate groups, wherein both directions of bonding to $R^4$ and $R^5$ are possible. For example, for the ester functionality, both $-R^4-C(O)O-R^5$, wherein $R^4$ is part of the acid portion of the ester, and $-R^4-OC(O)-R^5$, wherein $R^5$ is part of the acid portion of the ester, are included. When it is stated herein that either the $R^4$ or $R^5$ group is part of the acid portion of the ester, it is meant that such group, for example, was part of the acid halide precursor used (if an acid halide was used) in the formation of the monosubstituted dithiooxamide containing the ester group. It is noted, however, that the monosubstituted compounds incorporating $-R^4-OC(O)-R^5$, wherein $R^5$ is part of the acid portion of the ester, e.g., $H_2NC(S)C(S)NHR^4-OC(O)-R^5$, would be more readily synthesized from the methods outlined herein below. Similarly, monosubstituted compounds incorporating $-R^4-N(R^6)C(O)-R^5$, rather than the reversed functionality $-R^4-C(O)N(R^6)-R^5$, are generally more readily synthesized from the methods outlined below.

The parameters with respect to the sum of the number of carbons in $R^4$ and $R^5$ listed above generally result in the $R^3$ substituent imparting the desired volatility characteristics to the monosubstituted dithiooxamide compounds. This is apparent from the data presented in Tables 1 and 2, which indicate that nonvolatility results when such a parameter is a characteristic of the compound. For example, for the compound N-(6-propanoylamidohexyl)dithiooxamide, the number of carbons in $R^4$ equals 6, the number of carbons in $R^5$ equals 2, the total number of carbons in $R^4$ plus $R^5$ equals 8, and the compound is observed to be nonvolatile at 25° C.

Representative classes of compounds that meet the above-listed requirements include monosubstituted dithiooxamides in which the $R^3$ substituent is a long-chain alkyl or aralkyl group, or contains a carboxyl (i.e., an ester), amide, carbonate, carbamide, or carbamate functionality. Herein, the long-chain alkyl group may contain, for example, aromatic rings, branched structures, and groups containing heteroatoms. The aromatic ring, however, is not directly attached to the nitrogen of the dithiooxamide. General representations of the classes of compounds that are within the preferred classes include:

$H_2NC(S)C(S)NH-R^3$
$H_2NC(S)C(S)NH-R^4C(O)OR^5$
$H_2NC(S)C(S)NH-R^4OC(O)R^5$
$H_2NC(S)C(S)NH-R^4C(O)N(R^6)R^5$
$H_2NC(S)C(S)NH-R^4N(R^6)C(O)R^5$
$H_2NC(S)C(S)NH-R^4OC(O)OR^5$
$H_2NC(S)C(S)NH-R^4N(R^6)C(O)OR^5$
$H_2NC(S)C(S)NH-R^4OC(O)N(R^6)R^5$
$H_2NC(S)C(S)NH-R^4N(R^6)C(O)N(R^7)R^5$
$H_2NC(S)C(S)NH-R^4NR_2$

Therefore, it is understood that a wide variety of groups, or classes of compounds, are included within the general definition of the group R' in formula IX above. As mentioned previously, three general types of groups, however, are specifically excluded from being within the classes of preferred compounds identified by formula IX as defined when R' is specifically $R^3$. These are:

(a) aromatic groups wherein the amido nitrogen of the dithiooxamide structure is substituted directly onto the aromatic ring;
(b) groups wherein $R^3$ is sufficiently small and/or sufficiently polar to render the dithiooxamide water soluble and thus nonencapsulatable; and,
(c) groups wherein the resulting dithiooxamide would be sufficiently volatile at a temperature of about 25° C. to be undesirable in applications such as carbonless paper constructions.

The reasons why possible compounds as defined by paragraphs (b) and (c) are excluded are apparent from previous discussions. Compounds as defined by paragraph (a) are excluded from the class of preferred compounds as defined by IX above when R' is $R^3$ because the aromatic derivatives are generally colored in the uncomplexed state. Also, they generally exhibit a blue-green color upon coordination, rather than the preferred blue or blue-black color of the present invention. It is noted that blue-green polymer may have application in some instances, however. Also, in some instances, a colored ligand (noncomplexed) might be tolerable. Thus, while the recitation of preferred compounds according to the present invention excludes aromatic monosubstituted dithiooxamides, they are not to be understood as necessarily excluded from all aspects of the inventions described herein. In addition to the characteristic of relatively low volatility, compounds according to formula IX as defined are generally insoluble in aqueous solution, soluble in aqueous-immiscible solvents in a pH range of about 1 to 9, and thus are readily encapsulatable. Such aqueous-immiscible solvents include xylene, toluene, cyclohexane, diethyl phthalate, tributyl phosphate, and the like. Compounds included within the scope of formula IX as defined also generally readily form deep blue and/or blue-black images upon coordination with at least certain transition metal salts, and most preferably nickel salts.

Several examples of compounds according to formula IX when R' is $R^3$ as defined above include:
N-dodecyldithiooxamide
N-tetradecyldithiooxamide
N-hexadecyldithiooxamide
N-octadecyldithiooxamide
N-(2-octanoyloxyethyl)dithiooxamide
N-(2-decanoyloxyethyl)dithiooxamide
N-(2-dodecanoyloxyethyl)dithiooxamide
N-(2-hexanoylamidoethyl)dithiooxamide
N-(2-octanoylamidoerhyl)dithiooxamide
N-(6-propanoylamidohexyl)dithiooxamide
N-(6-butanoylamidohexyl)dithiooxamide
N-(1-naphthylmethyl)dithiooxamide
N-(11-carboxydecyl)dithiooxamide One preferred group of compounds for use in carbonless paper systems or systems in which a blue or blue-black image is desired is the group comprising monosubstituted dithiooxamide compounds with long-chain alkyl or aralkyl groups having 14 or more carbons. These compounds are generally nonvolatile at temperatures up to about 49° C. Example of compounds within this group are N-tetradecyldithiooxamide, N-hexadecyldithiooxamide, and N-octadecyldithiooxamide.

Another preferred group of compounds for use in systems as mentioned above are monosubstituted dithiooxamides with amide functionalities according to the formula $R^4-Y-R^5$ defined above wherein Y is $-N(R^6)C(O)-$, or with ester, i.e., carboxyl, functionalities according to the formula $R^4-Y-R^5$ defined above wherein Y is $-OC(O)-$. As stated above, these compounds containing $R^4-Y-R^5$ wherein Y is $-OC(O)-$ or $-N(R^6)C(O)-$, rather than the reversed functionalities $-(O)CO-$ or $-C(O)N(R^6)-$, are generally more readily synthesized from the methods outlined below. Examples of the preferred compounds within these classes of compounds are as follows:
N-(2-octanoyloxyethyl)dithiooxamide
N-(2-decanoyloxyethyl)dithiooxamide
N-(2-dodecanoyloxyethyl)dithiooxamide
N (2-octanoylamidoethyl)dithiooxamide
N-(2-hexanoylamidoethyl)dithiooxamide
N-(6-octanoylamidohexyl)dithiooxamide
N-(6-undecanoylamidohexyl)dithiooxamide
N-(5-propanoylamido-2-methylpentylldithiooxamide*
N-(5-propanoylamido-4-methylpentyl)dithiooxamide*
N-(5-pentanoylamido-2-methylpentyl)dithiooxamide*
N-(5-pentanoylamido-4-methylpentyl)dithiooxamlde*
N-(5-heptanoylamido-2-methylpentyl)dithiooxamide*
N-(5-heptanoylamido-4-methylpentyl)dithiooxamide*
N-(5-octanoylamido-2-methylpentyl)dithiooxamide*
N-(5-octanoylamido-4-methylpentyl)dithiooxamide*
N-(5-nonanoylamido-2-methylpentyl)dithiooxamide*
N-(5-nonanoylamido-4-methylpentyl)dithiooxamide*
N-(6-propanoylamidohexyl)dithiooxamide
N-(6-butanoylamidohexyl)dithiooxamide
N-(6-phenylacetamidohexyl)dithiooxamide
N-(12-propanoylamidododecyl)dithiooxamide
N-(12-octanoylamidododecyl)dithiooxamide
N-(2-phenylacetamidoethyl)dithiooxamide

*NOTE: These dithiooxamides were prepared as mixtures of the 2-methylpentyl and the 4-methylpentyl products, each with their respective optical isomers, since a mixture would result from typical synthesis methods described herein, more specifically as a result of the diamine used in the formation of the reactive amine. This diamine, 1,5-diamino-2-methylpentane, can result in the formation of two distinct products. For a further explanation of this, see the Experimental Section.

Those compounds that are relatively nonvolatile at temperatures of at least about 49° C., and preferably up to at least about 71° C., are particularly useful in the embodiments of the invention. Included within this group of most preferred compounds are monosubstituted dithiooxamides according to formula IX above, wherein $R^3$ is: an alkyl or aralkyl group having 18 or more carbon atoms; or a group of the structure —R-

⁴Y—R⁵ wherein Y is —N(R⁶)C(O)—, R⁶ is hydrogen or an alkyl or aralkyl group having 1 to 12 carbon atoms, R⁴ is a divalent alkyl or divalent aralkyl group having 1 to 12 carbon atoms, R⁵ is hydrogen or an alkyl or aralkyl group having 1 to 20 carbon atoms, and the total number of carbon atoms in R⁴ and R⁵ taken together is at least 8. This includes:

N-octadecyldithiooxamide
N-(6-propanoylamidohexyl)dithiooxamide
N-(2-octanoylamidoethyl)dithiooxamide
N-(6-butanoylamidohexyl)dithiooxamide
N-(6-octanoylamidohexyl)dithiooxamide
N-(6-undecanoylamidohexyl)dithiooxamide
N-(5-propanoylamido-2-methylpentyl)dithiooxamide*
N-(5-propanoylamido-4-methylpentyl)dithiooxamide*
N-(5-pentanoylamido-2-methylpentyl)dithiooxamide*
N-(5-pentanoylamido-4-methylpentyl)dithiooxamide*
N-(5-heptanoylamido-2-methylpentyl)dithiooxamide*
N-(5-heptanoylamido-4-methylpentyl)dithiooxamide*
N-(5-octanoylamido-2-methylpentyl)dithiooxamide*
N-(5-octanoylamido-4-methylpentyl)dlthiooxamide*
N-(5-nonanoylamido-2-methylpentyl)dithiooxamide*
N-(5-nonanoylamido-4-methylpentyl)dithiooxamide*
N-(6-phenylacetamidohexyl)dithiooxamide
N-(12-propanoylamidododecyl)dithiooxamide
N-(12-octanoylamidododecyl)dithiooxamide
N-(2-phenylacetamidoethyl)dithiooxamide

*NOTE: Products were actually prepared and isolated as mixtures of the 2-methylpentyl and 4-methylpentyl derivatives, with their respective optical isomers, of each amido-substituted dithiooxamide.

Again, the term "nonvolatile", when used with respect to monosubstituted dithioxamides according to the present invention, is meant to refer to compounds that pass the volatility test outlined herein below. That is, the compounds are classifiable as nonvolatile under the conditions of the test.

The above-listed compounds, and related compounds according to the general formula IX, are readily obtainable through synthetic methods described herein below, and more specifically via the preferred and advantageous methods described in copending U.S. patent application Ser. No. 07/438,765. It is understood that the above-listed compounds, and related compounds according to the general formula IX, include within their scope isomers, such as optical isomers.

The preferred compounds listed above generally form a dark blue or blue-black image upon coordination with nickel(II). It is noted that the presence of the N,N'-(dialkylsubstituted)dithiooxamide compound results in a redder image when a mixture of the two dithiooxamides (monoalkylsubstituted and dialkylsubstituted) is coordinated with nickel(II). It may be desirable in some instances, as for example due to purification and separation difficulties, to encapsulate the mixture of N-(monoalkylsubstituted) and N,N'-(dialkylsubstituted)dithiooxamides as formed (i.e., without separation and isolation of the monosubstituted product). Such a mixture (monoalkylsubstituted with minor amounts of dialkylsubstituted) is usable when reddish-blue images are desired.

The derivatized dithiooxamides containing both ester and/or amide functionality do not form mixtures that are difficult to purify, such as emulsions, upon large scale preparation. Therefore purification techniques are more facile for these compounds than for long-chain alkyls. However, the presence of N,N'-(dialkanoyloxyalkylsubstituted)dithiooxamide or N,N'-(dialkanoylamidoalkylsubstituted)dithiooxamide products may result in a bluer color when a mixture of the two dithiooxamides (mono- and di-substituted) is coordinated with nickel(II). It may, therefore, be desirable to encapsulate the mixture of these N-(monosubstituted-)and N,N'-(disubstituted)dithiooxamides as formed, without separation of the two products for use in, for example, carbonless paper constructions when a bluer image is preferred.

Upon review of the data in Tables 3 and 6 herein below, it is apparent that mixtures of N-(monoalkanoylamidoalkylsubstituted)dithiooxamides with N,N'-(dialkanoylamidoalkylsubstituted)dithiooxamides provide a blue image upon coordination with a transition metal cation having a +2 oxidation state such as $Ni^{+2}$. When such mixtures are used, a blue image is formed even when up to about 60 wt-% (relative to the total amount of mono- and di-substituted dithiooxamide) of the disubstituted dithiooxamide is present in the mixture. It is further noted that these mixtures may also contain optical isomers of the named compounds.

The invention also includes within its scope certain carbonless transfer constructions utilizing an N-(monosubstituted)dithiooxamide compound coated on a donor substrate surface for use as a reactant. The N-(monosubstituted)dithiooxamide compound used in this carbonless paper construction may be volatile or nonvolatile. Preferably, however, the N-(monosubstituted)-dithiooxamide compound used in this construction has the formula:

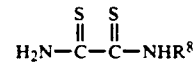

wherein: $R^8$ is a suitable group such that the dithiooxamide compound is substantially nonvolatile at about 25° C.

$R^8$ may be an aromatic group, if a colored ligand and a blue-green complex are acceptable. However, more preferably $R^8$ is as defined above for R', and most preferably $R^8$ is as defined for $R^3$. It is further noted that in the carbonless transfer constructions, not only is it possible to encapsulate the uncharged dithiooxamide compound, but it might also be possible to encapsulate the charged dithiooxamide compound. For example, a dithiooxamide compound with two amide hydrogens removed (one from each amide group) and an overall charge of $-2$, could then be stabilized with a $+2$ cation and encapsulated. The $+2$ cation would be one that is readily displaced from the dithiooxamide by the transition metal cation for image formation.

The present invention includes within its scope certain polymer complexes formed from monosubstituted dithiooxamides. Thus, the present invention encompasses within its scope polymers with the general formula $(ML)_n$ wherein M is a transition metal cation having an oxidation state of $+2$, preferably a cation selected from the group consisting of $Ni^{+2}$, $Zn^{+2}$, $Pd^{+2}$, $Pt^{+2}$, $Cu^{+2}$, $Fe^{+2}$, $Cd^{+2}$, $Hg^{+2}$, $Pb^{+2}$, and $Co^{+2}$; and, L is a dithiooxamide ligand according to the general formula IX wherein two amide hydrogens have been removed, one from each amide group, rendering an overall charge of $-2$, as in the following representation.

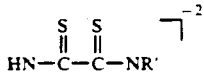

Preferably, R' in the above representation of the dithiooxamide ligand is $R^3$ as defined above.

In general, formation of the polymer complexes is a matter of reacting an N-(monosubstituted)dithiooxamide compound, with at least one molar equivalent and preferably a large excess, of a transition metal salt, preferably a salt of a +2 transition metal cation. The presence of a weak base, such as triethylamine, facilitates the reaction since it facilitates the removal of the amide protons from the dithiooxamide. Alternatively, the anion associated with the transition metal cation may facilitate removal of the amide protons. The generation of a blue or blue-black color is generally indicative of polymer formation.

In a typical application, to generate a dark image on a substrate, the polymer complex is formed by contacting the dithiooxamide (or a solution containing the dithiooxamide) with a substrate having a coating of transition metal salt thereon. The preferred transition metal salts are those of nickel; however, salts of copper, iron, and other transition metals may, in certain applications, be used within the scope of this invention. Examples of transition metal salts for this application are nickel 2-ethylhexanoate, nickel rosinate, nickel stearate, nickel benzoate, nickel 2-phenylbutyrate, nickel oleate, nickel hydrocinnamate, nickel calcium rosinate, and the like; see Lange, vide infra. Preferred transition metal salts for use in this invention are nickel rosinate, nickel 2-hexanoate, and mixtures thereof. Again, formation of the polymer complex is evidenced by appearance of a dark blue or blue-black color shortly after the imaging impact takes place.

The N-(monosubstituted)dithiooxamide compound used in the formation of the image may be volatile or nonvolatile. In preferred applications, however, it is a nonvolatile compound according to formula IX, and most preferably, it is a compound wherein R' of formula IX is $R^3$ as previously defined. The formation of the image may also include transferring an N,N'-(disubstituted)dithiooxamide compound to the substrate with the transition metal salt coated thereon, along with an effective amount of the N-(monosubstituted)dithiooxamide compound.

It is noted that complexes formed with dithiooxamides according to formula IX are relatively stable. Further, even if some reversal of coordination does occur, the relatively nonvolatile N-(monosubstituted)-dithiooxamides will remain on the surface of the receptor sheets, and thus recoordinate.

Carbonless Imaging Constructions

The invention further includes within its scope image transfer systems or constructions, i.e., carbonless impact marking papers for the transfer of images and methods of forming the images. In general, this involves coating one reactant, the dithiooxamide, on one substrate, and the transition metal salt (the other reactant) on another, mating, substrate. Means preventing reaction of the two until intended, i.e., until activating pressure is applied, are also provided. Preferably, dithiooxamide compound is contained or encapsulated in microcapsules on one sheet of paper. The reactant for the dithiooxamide compound, i.e., the transition metal salt, is carried on a mating sheet of paper. The microcapsules serve the purpose of isolating the reactants from one another (i.e., preventing reaction) until such time as pressure is applied to the paper for the purpose of creating an image.

Generally, a carbonless paper construction comprises at least two substrates, for example two sheets of paper, each with one surface, or side, coated with one of the two primary reactants. The two substrates are generally referred to as a donor sheet and a receptor sheet. When the coated faces, or surfaces, of the two substrates come into contact under sufficient pressure so that the reactants can mix, a reaction occurs and an image forms on the receptor sheet.

A preferred construction 1 (FIG. 1) comprises the encapsulated dithiooxamide compound dissolved in an appropriate solvent(s) within microcapsules and coated onto a back side 2 of a donor sheet 3 in a suitable binder. The back side 2 of donor sheet 3 is sometimes referred to herein as a coated back (CB) sheet 4. The metal salt, preferably a $Ni^{+2}$ salt, optionally in a suitable binder, is coated onto a front side 10 of a mating, or receptor, sheet 11, herein sometimes referred to as a coated front (CF) sheet 12. As stated previously, in imaging, the two sheets are positioned such that the back side 2 of donor sheet 3 faces the metal salt coating on the front side 10 of the receptor sheet 11 as shown in FIG. 1. When activating pressure is applied to face 15 of the donor sheet 3, the capsules rupture and release the dithiooxamide compound for transfer to the receptor sheet 11, forming a colored pattern due to complexing with the salt. It is noted that in FIG. 1 the coated back (CB) sheet 4 and the coated front (CF) sheet 12 are shown partially separated to facilitate understanding of the invention. Herein, "activating pressure" includes, but is not limited to, pressure applied by hand with a stylus or pressure applied by a business machine key, for example a typewriter key.

Also included within the scope of the invention is a construction comprising: a plurality of first substrate surfaces, each on which is coated the encapsulated N-(monosubstituted)dithiooxamide; and, a plurality of second substrate surfaces, each on which is coated a salt of a transition metal cation with a +2 oxidation state. Each of the coated first substrate surfaces is positioned within the construction in contact with one of the coated second substrate surfaces. Such a construction is known as a form set construction.

Substrates, with one surface on which is coated the encapsulated N-(monosubstituted)dithiooxamide, and a second, opposite, surface on which is coated a salt of a transition metal cation (as for example $Ni^{+2}$) can be placed between the CF and CB sheets, in a construction involving a plurality of substrates. Such a sheet is sometimes referred to as a CFB sheet. Of course, each side including the dithiooxamide thereon should be placed in juxtaposition with a sheet having metal salt thereon. CFB sheets are typically used in form sets.

Preparation of Substrate (Donor Sheet) Coated with Encapsulated N-(Monosubstituted)dithiooxamide A carbonless copy construction comprises a substrate containing microcapsules filled with a dithiooxamide compound dissolved in a suitable fill solvent or solvents, the solution of which is water-insoluble. Preferably, the shell of the capsules are of a water-insoluble urea-formaldehyde product formed by acid-catalyzed polymerization of a urea-formaldehyde precondensate; see G. W.

Matson, U.S. Pat. No. 3,516,846 (1970), incorporated herein by reference.

A capsule slurry, as prepared from a mixture of the urea-formaldehyde precondensate and a dithiooxamide-containing fill material, is combined with a binding agent, such as aqueous sodium alginate, starch, or latex, for coating on one face of a substrate. In the preferred embodiment, the back of the donor sheet is coated with the capsule slurry, and is referred to as the coated back (CB) sheet.

Preparation of Substrate (Receptor Sheet) Coated with Metal Salt

The receptor sheet with the transition metal salt coated thereon, or the developer sheet, comprises the transition metal salts of organic or inorganic acids. The preferred transition metal salts are those of nickel, although copper, iron, and other transition metals may be used to advantage in some applications.

Inorganic acids that can be used to react with the transition metals to form the transition metal salts are acids whose anions form salts with transition metals and that will dissociate from the transition metal in the presence of the dithiooxamide for the color-forming reaction. Typical inorganic acids are nitric acid and sulfuric acid, which form nickel nitrate and nickel sulfate, respectively.

Organic acids that are useful in forming the transition metal salts, and that readily dissociate in the presence of dithiooxamide ligands, are the aliphatic and aromatic mono- and di- carboxylic acids, substituted aliphatic and aromatic monocarboxylic acids, and heterocyclic monocarboxylic acids. Monocarboxylic aliphatic acids containing about 6 to 20 carbon atoms are preferred. Nickel 2-ethylhexanoate is a particularly preferred color-forming transition metal salt. Other representative transition metal salts are the nickel, iron, and copper salts of the described organic acids. Examples of such are nickel rosinate, nickel calcium rosinate, nickel stearate, nickel 2-phenylbutyrate, nickel oleate, nickel benzoate, and nickel hydrocinnamate, as well as the copper and iron analogues. Also, included within the scope of the invention are mixtures of these compounds.

The composition including the transition metal salt may be coated on substrates by conventional coating techniques. The transition metal salt is preferably coated on the front side of a substrate, such as a sheet of paper which is referred to as the coated front (CF) sheet. Additionally, the transition metal salt may be formulated into printing compositions and be printed onto all or a portion of a substrate, such as paper. See, for example, H. E. Lange, U.S. Pat. No. 4,111,462 (1978).

Evaluation of Volatility

The class of novel compounds defined according to the present invention exhibits a preferred volatility level, and thus its members are generally useable in carbonless imaging transfer systems such as the preferred ones described above, in which selected formation of a blue or blue-black, i.e., dark, image is desired. The method utilized in the experiments to both define and evaluate the level of volatility was as follows. A piece of Grade #10 (20×12) cheesecloth was placed between a simulated donor sheet and a receptor sheet of a carbonless paper construction. The simulated donor sheet comprised a sheet of dithiooxamide-saturated paper, which was used to simulate a CB sheet with ruptured capsules. Pressure was then applied for 24 hours by placing 9 pounds of paper on top of the sheets, to simulate storage conditions of the paper packages. The formation of color on the receptor sheet, due to transfer of volatile dithiooxamides thereto, was used as an indication that the particular dithiooxamide was not desirable for carbonless paper constructions, i.e., was volatile. A compound was considered generally to be nonvolatile, within the meaning of the term as used herein to define the present invention and thus to define monosubstituted dithiooxamides acceptable for use in carbonless image transfer arrangements, if no color was formed after the simulated test was run for about 24 hours at 25° C. In some instances, if no color was formed after storage at room temperature (25° C.), successively higher temperatures were used, as for example 49° C., 60° C., and 71° C. This will be better understood by reference to Experiment 14 below. In general, the most preferred compounds, with respect to volatility, are those which do not substantially generate color appearance under the conditions of the test, even at the higher temperatures.

Determination of Complex Color

In general, the colors of the complexes were determined by preparing a solution of the dithiooxamide and appropriate solvent, and then applying the solution to a substrate coated with a $Ni^{+2}$ salt, by means of an application swab. Rapid and complete development of the image was enhanced by passing the sheet through a hot shoe adjusted to 102° C. Visually observed colors were recorded.

One method of color measurement is to determine the color's position in color space. One color space system is the Hunter System; see F. W. Billmeyer, Jr., and M. Saltzman, *Principles of Color Technology;* John Wiley & Sons; New York, N.Y.; Ch. 2 and 3, 1981. In this system three mutually perpendicular axes (L, a, and b) are needed to define a color. "L" (+z axis) represents the color intensity; "a" (x axis) represents the amount of red or green (+a is red, −a is green); and "b" (y axis) represents the amount of yellow or blue (+b is yellow, −b is blue). By measuring a material's L, a, and b values, the color of one sample can be compared with that of other samples. Because the color of a sample is also dependent upon the color temperature of the illuminating source, the angle at which the sample is illuminated, the angle at which the illumination is reflected, and the angle of the retina illuminated, these all need to be specified. Many instruments have been developed to record these values. One such instrument is the HunterLab LabScan II. This instrument is capable of automatically determining the L, a, and b values for a given sample, and was used for the following examples.

The present invention will be further described by reference to the following detailed examples.

EXPERIMENTAL EXAMPLES

As the following experiments show, according to the present invention, there is defined a class of N-(monosubstituted)dithiooxamides useable in the formation of a dark blue or blue-black complex upon association with a transition metal cation. The complex is not only of the preferred color, but also the class of compounds according to the invention is relatively nonvolatile and thus readily useable in products for which a blue or blue-black image is preferred, such as carbonless paper constructions.

EXPERIMENT 1

Synthesis of N-Dodecyldithiooxamide

The yield of N-(monosubstituted)dithiooxamides can be improved in certain circumstances by conducting the transamination (Wallach) reaction in the presence of a weak, nonreactive, nitrogen base, such as aniline or pyridine. The present reported synthesis corresponds to such procedure. It was used as a preferred method for synthesizing certain compounds according to the present invention.

Into a 100 ml round-bottomed flask, equipped with a magnetic stirrer and heating bath, were placed 2.4 g (0.02 mol) of dithiooxamide, 1.8 g (0.02 mol) of aniline, and 40 ml of methanol. The solution was stirred and heated at 35° C. for 30 minutes. The reactive amine, dodecylamine (3.7 g, 0.02 mol), was then added, and the solution was stirred for an additional 3 hours at 35° C. The crude reaction mixture was cooled to 25° C., and the acidity was adjusted to a pH of about 2 by the addition of 37% aqueous HCl. The mixture was filtered, washed with a small amount of methanol, and dried to afford 1.5 g of N,N'-didodecyldithiooxamide. Water (40 ml) was added to the filtrate with stirring, which was continued for 10 minutes. The precipitate was collected by filtration and washed with a minimum amount of a 50:50 mixture of water and methanol. The product was dried to afford 3.2 g (55%) of N-dodecyldithiooxamide.

EXPERIMENT 2

Synthesis of N-(2-Octanoyloxyethyl)dithiooxamide

Into a 250 ml round-bottomed flask, equipped with a rotary stirrer, condenser, and heating bath, were placed 6.0 g (0.05 mol) of dithiooxamide and a solution of pyridine (4.0 g, 0.05 mol) dissolved in methanol (100 ml). The solution was heated, with stirring, at 35° C. for 30 minutes. The reactive amine, ethanolamine (3.0 g, 0.05 mol), was added, and the mixture was stirred and heated at 35° C. for 3 hours. The crude reaction mixture was cooled to room temperature. The acidity of this mixture was adjusted to a pH of about 2 by the addition of 37% aqueous HCl. The methanol was removed in vacuo, and 100 ml of methylene chloride was added. The resultant mixture was stirred at room temperature for 30 minutes. Unreacted dithiooxamide (3 g) was removed as a dark brown solid by filtration of the mixture.

The filtrate containing N-(2-hydroxyethyl)dithiooxamide was collected and the solvent was removed in vacuo. Octanoyl chloride (8.0 g, 0.05 mol) was added to the resultant oil. The reaction mixture was heated at 60° C. for 1 hour, cooled to room temperature, and 100 ml of a 50:50 mixture of methanol and water was added. Sodium bicarbonate was then added until the solution pH was about 7. The mixture was then filtered, affording 4.5 g of N,N'-di(2-octanoyloxyethyl)dithiooxamide. The filtrate from this step was extracted with methylene chloride (2×50 ml), transferred to a round-bottomed flask and dried over magnesium sulfate. Solvent was removed at reduced pressure, affording 7.0 g (50%) of N-(2-octanoyloxyethyl)dithiooxamide as a dark black oil. The material was 80% pure as determined by gas chromatography.

In general, monosubstituted dithiooxamide compounds containing a substituent with an ester linkage can be synthesized by this method. That is, an N-(hydroxyalkyl) dithiooxamide compound is synthesized initially, followed by the derivatization with an acyl halide to afford an N-(acyloxyalkyl)dithiooxamide.

EXPERIMENT 3

Preparation of 2-Octanoylamidoethylamine

This compound was prepared as described in Japan Patent 67: 15,925, incorporated herein by reference, and was used as the reactive amine in the formation of N-(2-octanoylamidoethyl)dithiooxamide (see Experiment 4). Specifically, into a 250 ml round-bottomed flask, equipped with a condenser, magnetic stirrer, and heating mantle, were placed 100 g (0.82 mol) of octanenitrile, 50 g (0.82 mol) of ethylenediamine, 0.4 g of sulfur, and 20 g of water. The mixture was heated at reflux for 20 hours, and then allowed to cool to room temperature. The condenser was removed, replaced by a distillation head, and 1.0 g (0.015 mol) of powdered zinc was added. Water and ethylene diamine were removed in vacuo and the product was distilled to afford 124 g (81%) of 2-octanoylamidoethylamine; bp 155°–157° C. (0.25 mm Hg). The material partially solidified upon standing. This compound was identified by NMR spectroscopy.

EXPERIMENT 4

Preparation of N-(2-Octanoylamidoethyl)dithiooxamide

Into a 100 ml round-bottomed flask, equipped with rotary stirrer, condenser, and heating bath, were placed 2.4 g (0.02 mol) of dithiooxamide, 1.8 g (0.02 mol) of aniline, and 40 ml of methanol. The reaction was heated at 35° C. for 30 minutes. To this solution 3.8 g (0.02 mol) of 2-octanoylamidoethylamine, as prepared according to Experiment 3, was added, and the reaction mixture was maintained at 35° C. for 3 hours. The crude reaction mixture was cooled to room temperature, and the acidity was adjusted to a pH of about 2 by the addition of 37% HCl (aqueous). A white solid precipitated, identified as an imidazoline, and was collected by filtration. Water (40 ml) was added to the filtrate to precipitate the product as a brown solid. Stirring for 30 minutes was followed by filtration and drying to afford 1.8 g (31%) of N-(2-octanoylamidoethyl)dithiooxamide. Analysis by thin layer chromatography verified virtually no disubstituted product.

EXPERIMENT 5

Preparation of 1-Amino-6-propanoylamidohexane

The reactive amine used in the formation of N-(6-propanoylamidohexyl)dithiooxamide (see Experiment 6) was made in the following manner. Into a pressure reaction kettle were placed 90.90 kg ($7.8 \times 10^2$ mol) of 1,6-hexanediamine. Propionic acid (29.09 kg, $3.9 \times 10^2$ mol) was added and the reaction mixture heated under ambient pressure at 150° C. for 6 hours. Upon cooling, a vacuum was attached and the reaction mixture was again heated. Excess 1,6-hexanediamine was distilled off between 100°–140° C. at 5 mm Hg. The amount of recovered 1,6-hexanediamine was approximately 50 kg. The condenser was maintained at 50° C. to prevent solidification of the diamine upon cooling. Continued vacuum distillation between 140°–160° C. at 0.25 mm Hg afforded 45 to 54 kg of 1-amino-6-propanoylamidohexane as a clear to pale yellow oil The yield was in the range of 65–80%. This material partially solidified upon standing.

The purity of 1-amino-6-propanoylamidohexane was evaluated by gas chromatography in the following manner. A small amount of the reaction product was dissolved in chloroform. The solution was injected onto a capillary DB-1 column 15 m in length, with an inside diameter of 0.25 mm and a 0.00025 mm film thickness. The initial column temperature was 75° C., which was held for 2 minutes. The temperature was then raised 15° C./minute until a temperature of 250° C. was reached. This temperature was maintained for 5 minutes. The retention time for 1-amino-6-propanoylamidohexane was 7.70 minutes and that for 1,6-dipropanoylamidohexane was 11.5 minutes. The retention time of unreacted 1,6-hexanediamine was 2.68 minutes. Integration of the gas chromatography data indicated that the following amounts of material were present: unreacted 1,6-hexanediamine (50–55%), 1-amino-6-propanoylamidohexane (35–40%), and 1,6-dipropanoylamidohexane (5–10%). IR and NMR ($^1$H and $^{13}$C) spectra were in agreement with the assigned structures.

EXPERIMENT 6

Preparation of N-(6-Propanoylamidohexyl)dithiooxamide

Into a reaction kettle equipped with rotary stirrer, condenser, and heating bath were placed 16.36 kg (1.4 × 10$^2$ mol) of dithiooxamide, 218 kg of methanol, and 28 kg of aniline. The reaction mixture was heated and maintained at a temperature of 35° C. for 30 minutes. The reactive amine, 1-amino-6-propanoylamidohexane (16.36 kg, 95 mol), was added and the reaction mixture was maintained at a temperature of about 35° C. for 2 hours. An additional 6.19 kg (36 mol) of 1-amino-6-propanoylamidohexane was added and the reaction was allowed to continue for an additional 4 hours. The reaction mixture was cooled to 25° C. The acidity was adjusted to a pH of below about 3 by addition of approximately 60 kg of 37% HCl (aqueous). A vacuum was attached to the kettle, heating was begun and the methanol was removed. The temperature was maintained below 40° C. throughout the vacuum distillation. Dichloromethane (181 kg) was added to the resultant oil. This was followed by the addition of 136 kg of water. The mixture was pressure filtered through a bag or Quno filter and the phases allowed to separate. Collection of the lower organic phase followed by solvent removal at reduced pressure afforded a mixture of N-(6-propanoylamidohexyl)dithiooxamide and N,N'-di(6,6'-propanoylamidohexyl)dithiooxamide.

Tributyl phosphate (18.2 kg) was added and the purity of the resultant mixture of N-(6-propanoylamidohexyl)dithiooxamide and N,N'-di(6,6'-propanoylamidohexyl)dithiooxamide was evaluated by liquid chromatography in the following manner. A small amount of the reaction mixture was dissolved in spectral grade acetonitrile. A 25 μl sample was injected onto a HP 1090 liquid chromatograph with a 15 cm × 4.6 mm endcapped C-8 IBM trimethylsilyl guard column. The sample was eluted with a gradient mixture of water and acetonitrile with 2 μmol of dibutylamine additive at a flow rate of 0.75 ml/min and at a temperature of 50° C. The run gradient time was 15 minutes. The gradient slope was 100% water at 0 minutes, 75% acetonitrile at 10 minutes, and 100% acetonitrile at 15 minutes. The uv detector was set at 305 nm. Dithiooxamide was found to elute at 5.5 minutes, N-(6-propanoylamidohexyl)dithiooxamide eluted at 9.5 minutes, and N,N'-di(6,6'-propanoylamidohexyl)dithiooxamide eluted at 10.9 minutes. The amount of N-(6-propanoylamidohexyl)dithiooxamide was found to be 11.1 kg (40 mol) and the amount of N,N-di(6,6'-propanoylamidohexyl)dithiooxamide was found to be 7.5 kg (17.4 mol). The mole ratio of the monosubstituted product to the disubstituted product was 2.3:1.

A sample of the reaction mixture was adsorbed onto a silica gel column and eluted with a 50:50 mixture of hexane/ethyl acetate. N-(6-propanoylamidohexyl)dithiooxamide eluted first, followed by N,N'-di(6,6'-propanoylamidohexyl)dithiooxamide. $^{13}$C NMR spectra of the thus purified samples of both N-(6-propanoylamidohexyl)dithiooxamide (the major product) and N,N'-di(6,6'-propanoylamidohexyl)dithiooxamide (formed as the minor product) were in agreement with the assigned structures.

EXPERIMENT 7

Preparation of N-benzyldithiooxamide

Into a 5 liter, 3-necked flask equipped with a mechanical stirrer, thermometer, and reflux condenser were placed 212 g (1.77 mol) of dithiooxamide (DTO), 2,200 g of methanol, and 224 g of deionized water. The reaction mixture was stirred and heated to reflux. At that point, 126 g (1.18 mol) of benzylamine, i.e., the reactive amine, was added. The progress of the reaction was monitored by thin layer chromatography (TLC) to detect the initial formation of N,N'-dibenzyldithiooxamide. After about 20 minutes, formation of the disubstituted product was detected and the reaction was quenched by the addition of 100 g of concentrated HCl.

The reaction mixture was transferred to a round-bottomed flask. The methanol was removed under reduced pressure. Water and benzene (1,000 g each) were added and after thorough mixing, the mixture was filtered to remove unreacted DTO. The amount of DTO recovered was 99 g (0.825 mol). Removal of the lower aqueous layer was followed by the addition of 1,000 g of water and 100 g of concentrated HCl. Transfer of the two-phase mixture to a round-bottomed flask was followed by solvent removal under reduced pressure. As the benzene was removed, the product precipitated. Filtration and air drying afforded 170 g of crude product.

A portion of the mixture was separated into its components by flash chromatography on silica gel and eluted with 10% ethyl acetate in hexanes. N,N'-dibenzyldithiooxamide eluted first, followed by N-benzyldithiooxamide. The product ratio of N,N'-dibenzyldithiooxamide to N-benzyldithiooxamide was 1:3.

EXPERIMENT 8

In a manner analogous to the procedure reported for Experiment 1 above, the following N-(monosubstituted)dithiooxamides were prepared:
N-octadecyldithiooxamide
 (reactive amine = octadecylamine)
N-tetradecyldithiooxamide
 (reactive amine = tetradecylamine)
N-hexadecyldithiooxamide
 (reactive amine = hexadecylamine)
 N-methyldithiooxamide was prepared as described in B Persson et al., *Acta Chem. Scand.*, 1964, 18, 1059.

In a manner analogous to that reported for Experiment 7 above, the following N-(monosubstituted)dithiooxamides were prepared. In many cases, chromatography was not necessary and the N-(monosubstituted)dithiooxamide could be purified and isolated by recrystalization of the precipitated mixture from solvents such as ethanol, isopropanol, ethyl acetate or mixtures thereof.

N-octyldithiooxamide
  (reactive amine = octylamine)
N-butyldithiooxamide
  (reactive amine = butylamine)
N-decyldithiooxamide
  (reactive amine = decylamine)
N-(4-methylbenzyl)dithiooxamide
  (reactive amine = 4-methylbenzylamine)
N-(4-dimethylaminobenzyl)dithiooxamide
  (reactive amine = 4-dimethylaminobenzylamine)
N-(3,4-dichlorobenzyl)dithiooxamide
  (reactive amine = 3,4-dichlorobenzylamine)
N-cyclopropyldithiooxamide
  (reactive amine = cyclopropylamine)
N-(4-methoxybenzyl)dithiooxamide
  (reactive amine = 4-methoxybenzylamine)
N-(11-carboxydecyl)dithiooxamide
  (reactive amine = 11-carboxydecylamine)
N-(4-chlorobenzyl)dithiooxamide
  (reactive amine = 4-chlorobenzylamine)
N-(2-phenylethyl)dithiooxamide
  (reactive amine = 2-phenylethylamine)
N-(1-naphthylmethyl)dithiooxamide
  (reactive amine = 1-naphthylmethylamine)

N-(3-diethylaminopropyl)dithiooxamide was synthesized from 3-(diethylaminopropyl)isothiocyanate (purchased from Fairfield Chemical Company, Blythewood, S.C.), potassium cyanide, and hydrogen sulfide in a water/glyme mixture [see for example, A. D. Grabenko et al., Zhur. Obshch. Khim. 1960, 30, 1222 or J. F. Olin, U.S. Pat. No. 3,318,675 (1967)]. Similarly, N-ethyldithiooxamide was synthesized from ethyl isothiocyanate.

Using the general procedure outlined in Experiment 2, N-(2-dodecanoyloxyethyl)dithiooxamide was synthesized from N-(2-hydroxyethyl)dithiooxamide and dodecanoyl chloride, and N-(2-decanoyloxyethyl)dithiooxamide was synthesized from N-(2-hydroxyethyl)dithiooxamide and decanoyl chloride.

In a manner analogous to the procedure reported for Experiments 3 and 4, or 5 and 6, above, the following N-(monosubstituted)dithiooxamides were prepared:

N-(2-hexanoylamidoethyl)dithiooxamide
  (reactive amine = 2-hexanoylamidoethylamine)
N-(6-butanoylamidohexyl)dithiooxamide
  (reactive amine = 1-amino-6-butanoylamidohexane)
N-(2-acetamidoethyl)dithiooxamide
  (reactive amine = 2-acetamidoethylamine)
N-(6-phenylacetamidohexyl)dithiooxamide
  (reactive amine = 1-amino-6-phenylacetamidohexane)
N-(12-propanoylamidododecyl)dithiooxamide
  (reactive amine = 1-amino-12-propanoylamidododecane)
N-(12-octanoylamidododecyl)dithiooxamide
  (reactive amine = 1-amino-12-octanoylamidododecane)
N-(2-phenylacetamidoethyl)dithiooxamide
  (reactive amine = 2-phenylacetamidoethylamine)
N-(6-octanoylamidohexyl)dithiooxamide
  (reactive amine = 1-amino-6-octanoylamidohexane)
N-(6-undecanoylamidohexyl)dithiooxamide
  (reactive amine = 1-amino-6-undecanoylamidohexane)
N-(5-propanoylamido-2-methylpentyl)dithiooxamide mixed with N-(5-propanoylamido-4-methylpentyl)dithiooxamide*
  (reactive amine = mixture of 1-amino-2-methyl-5-propanoylamidopentane and 1-amino-4-methyl-5-propanoylamidopentane)
N-(5-pentanoylamido-2-methylpentyl)dithiooxamide mixed with N-(5-pentanoylamido-4-methylpentyl)dithiooxamide*
  (reactive amine = mixture of 1-amino-2-methyl-5-pentanoylamidopentane and 1-amino-4-methyl-5-pentanoylamidopentane)
N-(5-octanoylamido-2-methylpentyl)dithiooxamide mixed with N-(5-octanoylamido-4-methylpentyl)dithiooxamide*
  (reactive amine = mixture of 1-amino-2-methyl-5-octanoylamidopentane and 1-amino-4-methyl-5-octanoylamidopentane)
N-(5-heptanoylamido-2-methylpentyl)dithiooxamide mixed with N-(5-heptanoylamido-4-methylpentyl)dithiooxamide*
  (reactive amine = mixture of 1-amino-2-methyl-5-heptanoylamidopentane and 1-amino-4-methyl-5-heptanoylamidopentane)
N-(5-nonanoylamido-2-methylpentyl)dithiooxamide mixed with N-(5-nonanoylamido-4-methylpentyl)dithiooxamide*
  (reactive amine = mixture of 1-amino-2-methyl-5-nonanoylamidopentane and 1-amino-4-methyl-5-nonanoylamidopentane)

*NOTE: These dithiooxamides were all prepared as mixtures of the 2-methylpentyl and the 4-methylpentyl products because the diamine used in the formation of the reactive amine was 1,5-diamino-2-methylpentane. In the reaction between this diamine and the appropriate carboxylic acid, reaction between the amine group at the "1" position and the acid resulted in formation of the 4-methylpentyl product upon subsequent reaction with dithiooxamide. Similarly, the reaction of the amine group at the "5" position with the acid resulted in formation of the 2-methylpentyl product upon further reaction with dithiooxamide. Each of the 2-methylpentyl and 4-methylpentyl dithiooxamides have a chiral center. Therefore, these mixtures also include the optical isomers.

EXPERIMENT 9

Preparation of the Polymeric Complex $(NiL)_n$
(L = N-dodecyldithiooxamide minus 2 H-atoms)

Into a 250 ml round-bottomed flask were placed 0.288 g ($1.0 \times 10^{-3}$ mol) of N-dodecyldithiooxamide and 60 ml of absolute ethanol. The reaction mixture was stirred and heated until a temperature of 40° C. was reached. Upon dissolution of the ligand, a warm solution of 0.249 g (0.001 mol) of $Ni(OAc)_2 \cdot 4H_2O$ in 100 ml of ethanol was added. An immediate precipitate formed. The mixture was cooled to room temperature, and stirred for an additional 2 hours. The solid was collected by filtration and washed repeatedly with ethanol. Upon drying, a dark brown solid was obtained. The infrared spectrum of this material indicated the absence of the free amino groups present in the starting material.

EXPERIMENT 10

Preparation of the Polymeric Complex $(NiL)_n$
[L = N-(2-decanoyloxyethyl)dithiooxamide minus 2 H-atoms]

In a manner analogous to that described above, the polymer was prepared from 0.318 g ($1.0 \times 10^{-3}$ mol) of N-(2-decanoyloxyethyl)dithiooxamide and 0.249 g ($1.0 \times 10^{-3}$ mol) of $Ni(OAc)_2 \cdot 4H_2O$.

EXPERIMENT 11

Encapsulation of the N-(Monosubstituted)dithiooxamides and Preparation of the CB Sheet A precondensate solution was prepared comprising 191.88 g of formalin, 0.63 g of potassium tetraborate, 71.85 g of urea, and, 327.93 g of soft water. The formalin was 37% formaldehyde, and was added to a 1-liter flask equipped with a stirrer and heating mantle. The potassium tetraborate and urea were then added, and the mixture was heated to 70° C. The reaction was maintained at that temperature for 2.5–3.0 hours. The reaction mixture was then diluted with the water and allowed to cool. The precondensate solution, with about 24% solids, was then ready for use in the encapsulation process.

The precondensate and fill (dithiooxamide and carrier or fill solvents) were combined to make capsules according to the following procedure. Sodium chloride (29.54 g) was added to the stirred precondensate solution and the temperature of the solution was adjusted to 20° C. The fill material (214.17 g) was added and full agitation was begun. After 5 minutes of stirring, 10% hydrochloric acid solution was added over 5 minutes in an amount such that the final pH of the reaction mixture was about 2.8. The reaction mixture was stirred for another 12 minutes. More of the 10% hydrochloric acid solution was added over a period of 12 minutes, in an amount such that the final pH of the solution was about 1.8. The reaction mixture was stirred at 20° C. for 1 hour, and then at 60° C. for 1–3 hours. The acidic solution was allowed to cool and adjusted to a pH of 7 by addition of concentrated ammonium hydroxide solution (28%). The capsule slurry could then be stored for later use.

The capsule slurry (10 g) was added to 65 g of a 1.5% aqueous sodium alginate solution. The mixture was applied to a coated paper using a bar coater with a 3 mil gap. The coating was allowed to dry at room temperature.

EXPERIMENT 12

Determination of the Volatility of DTO Derivatives

The volatilities of the DTO derivatives were determined by preparing a 1% solution, by weight, of each substituted dithiooxamide (prepared as above-described) in acetone. Each solution was applied to bond paper (16 pound) with a cotton swab to saturate an area approximately 3 cm by 10 cm, and the acetone was allowed to evaporate by air drying for about 30 minutes. This treated paper, a simulated donor sheet, was then covered with a single layer of Grade #10 (20×12) cheesecloth (AF&F Item No. 588033, American Fiber and Finishing, Inc., Burlington, Mass.) and a receptor sheet was placed receptor side down on top of the cheesecloth. The receptor sheet was a white CF sheet manufactured by the Carbonless Products Department of 3M Company, St. Paul, Minn. Two reams of paper (9 pounds) were placed on the sheets to maintain intimate contact. After a selected time (approximately 24 hours) at room temperature, the CF sheet was removed and visually inspected for coloration. The results using this procedure are listed in Table 1. A similar test was conducted at elevated temperatures for several of the materials. The results of this analysis appear in Table 2. In these tables: "volatile" indicates that colored image was readily perceptible; "slightly volatile" indicates that colored image was barely perceptible, i.e., faint; and, "nonvolatile" indicates that there was no detectable colored image.

EXPERIMENT 13

Determination of Polymer Complex Colors

The colors of the polymer complexes, as listed in Tables 3–5, were determined by preparing a solution of the indicated concentration of each dithiooxamide in a solvent composed of a mixture of tributylphosphate (26.5%), diethylphthalate (17.6%), and cyclohexane (55.9%). The images were formed by applying two stripes of the substituted dithiooxamide solution to a Ni(II) coated receptor sheet using a cotton tipped applicator swab. Rapid and complete development of the image was achieved by passing the sheet through a hot shoe adjusted to 102° C., making a revolution every 10 seconds. The visually observed colors were recorded. The L, a, and b color coordinates of the more uniform stripe were measured for 45°/0° reflectance on a HunterLab LabScan II, secondary observer, using illuminant C. The observed (image) color and the Hunter coordinates are given in Tables 3–5 for Ni(II) complexes of the monosubstituted alkyl dithiooxamides, the monosubstituted aryl dithiooxamides, and the disubstituted alkyl dithiooxamides, respectively.

The invention has been described with reference to various specific and preferred embodiments and techniques. It should be understood, however, that many variations and modifications may be made while remaining within the spirit and scope of the invention.

TABLE 1

Room Temperature Volatility of N-Monosubstituted Dithiooxamides
$H_2NC(S)C(S)NHR$

| Ref. No. | Name of Compound | R | Volatility |
|---|---|---|---|
| 1 | N-methyldithiooxamide | $-CH_3$ | Volatile |
| 2 | N-ethyldithiooxamide | $-C_2H_5$ | Volatile |
| 3 | N-butyldithiooxamide | $-n-C_4H_9$ | Volatile |
| 4 | N-octyldithiooxamide | $-n-C_8H_{17}$ | Volatile |
| 5 | N-decyldithiooxamide | $-n-C_{10}H_{21}$ | Volatile |
| 6 | N-benzyldithiooxamide | 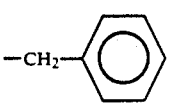 | Volatile |

TABLE 1-continued

Room Temperature Volatility of
N-Monosubstituted Dithiooxamides
$H_2NC(S)C(S)NHR$

| Ref. No. | Name of Compound | R | Volatility |
|---|---|---|---|
| 7 | N-(4-chlorobenzyl)dithiooxamide | $-CH_2-C_6H_4-Cl$ (para) | Volatile |
| 8 | N-(4-methylbenzyl)dithiooxamide | $-CH_2-C_6H_4-CH_3$ (para) | Volatile |
| 9 | N-(4-dimethylaminobenzyl)dithiooxamide | $-CH_2-C_6H_4-N(CH_3)_2$ (para) | Volatile |
| 10 | N-(3,4-dichlorobenzyl)dithiooxamide | $-CH_2-C_6H_3-Cl_2$ (3,4) | Volatile |
| 11 | N-(2-phenylethyl)dithiooxamide | $-CH_2CH_2-C_6H_5$ | Volatile |
| 12 | N-(2-hydroxyethyl)dithiooxamide | $-CH_2CH_2OH$ | Volatile |
| 13 | N-(2-acetamidoethyl)dithiooxamide | $-CH_2CH_2NHC(O)CH_3$ | Volatile |
| 14 | N-(3-diethylaminopropyl)dithiooxamide) | $-CH_2CH_2CH_2N(C_2H_5)_2$ | Volatile |
| 15 | N-cyclopropyldithiooxamide | $-HC(CH_2CH_2)$ (cyclopropyl) | Volatile |
| 16 | N-(4-methoxybenzyl)dithiooxamide | $-CH_2-C_6H_4-OCH_3$ (para) | *Sl. Vol. |
| 17 | N-dodecyldithiooxamide | $-(CH_2)_{11}CH_3$ | Nonvolatile |
| 18 | N-tetradecyldithiooxamide | $-(CH_2)_{13}CH_3$ | Nonvolatile |
| 19 | N-hexadecyldithiooxamide | $-(CH_2)_{15}CH_3$ | Nonvolatile |
| 20 | N-octadecyldithiooxamide | $-(CH_2)_{17}CH_3$ | Nonvolatile |
| 21 | N-(2-octanoyloxyethyl)dithiooxamide | $-CH_2CH_2OC(O)(CH_2)_6CH_3$ | Nonvolatile |
| 22 | N-(2-decanoyloxyethyl)dithiooxamide | $-CH_2CH_2OC(O)(CH_2)_8CH_3$ | Nonvolatile |
| 23 | N-(2-dodecanoyloxyethyl)dithiooxamide | $-CH_2CH_2OC(O)(CH_2)_{10}CH_3$ | Nonvolatile |
| 24 | N-(2-hexanoylamidoethyl)dithiooxamide | $-CH_2CH_2NHC(O)(CH_2)_4CH_3$ | Nonvolatile |
| 25 | N-(2-octanoylamidoethyl)dithiooxamide | $-CH_2CH_2NHC(O)(CH_2)_6CH_3$ | Nonvolatile |
| 26 | N-(1-naphthylmethyl)dithiooxamide | $-CH_2-$(naphthyl) | Nonvolatile |
| 27 | N-(11-carboxydecyl)dithiooxamide | $-(CH_2)_{10}COOH$ | Nonvolatile |
| 28 | N-(6-propanoylamidohexyl)dithiooxamide | $-(CH_2)_6NHC(O)CH_2CH_3$ | Nonvolatile |
| 29 | N-(6-butanoylamidohexyl)dithiooxamide | $-(CH_2)_6NHC(O)CH_2CH_2CH_3$ | Nonvolatile |
| 30 | N-(6-octanoylamidohexyl)dithiooxamide | $-(CH_2)_6NHC(O)(CH_2)_6CH_3$ | Nonvolatile |
| 31 | N-(6-undecanoylamidohexyl)dithiooxamide | $-(CH_2)_6NHC(O)(CH_2)_9CH_3$ | Nonvolatile |
| 32-33 | N-(5-propanoylamido-2-methylpentyl)-dithiooxamide mixed with N-(5-propanoylamido-4-methylpentyl)-dithiooxamide | $-CH_2CH(CH_3)(CH_2)_3NHC(O)CH_2CH_3$ $-(CH_2)_3CH(CH_3)CH_2NHC(O)CH_2CH_3$ | Nonvolatile |
| 34-35 | N-(5-pentanoylamido-2-methylpentyl)-dithiooxamide mixed with N-(5-pentanoylamido-4-methylpentyl)- | $-CH_2CH(CH_3)(CH_2)_3NHC(O)(CH_2)_3CH_3$ $-(CH_2)_3CH(CH_3)CH_2NHC(O)(CH_2)_3CH_3$ | Nonvolatile |

TABLE 1-continued

Room Temperature Volatility of
N-Monosubstituted Dithiooxamides
$H_2NC(S)C(S)NHR$

| Ref No | Name of Compound | R | Volatility |
|---|---|---|---|
| 36–37 | N-(5-heptanoylamido-2-methylpentyl)-dithiooxamide mixed with | $-CH_2CH(CH_3)(CH_2)_3NHC(O)(CH_2)_5CH_3$ | Nonvolatile |
|  | N-(5-heptanoylamido-4-methylpentyl)-dithiooxamide | $-(CH_2)_3CH(CH_3)CH_2NHC(O)(CH_2)_5CH_3$ |  |
| 38–39 | N-(5-octanoylamido-2-methylpentyl)-dithiooxamide mixed with | $-CH_2CH(CH_3)(CH_2)_3NHC(O)(CH_2)_6CH_3$ | Nonvolatile |
|  | N-(5-octanoylamido-4-methylpentyl)-dithiooxamide | $-(CH_2)_3CH(CH_3)CH_2NHC(O)(CH_2)_6CH_3$ |  |
| 40–41 | N-(5-nonanoylamido-2-methylpentyl)-dithiooxamide mixed with | $-CH_2CH(CH_3)(CH_2)_3NHC(O)(CH_2)_7CH_3$ | Nonvolatile |
|  | N-(5-nonanoylamido-4-methylpentyl)-dithiooxamide | $-(CH_2)_3CH(CH_3)CH_2NHC(O)(CH_2)_7CH_3$ |  |
| 42 | N-(6-phenylacetamidohexyl)-dithiooxamide | $-(CH_2)_6NHC(O)-CH_2-\text{C}_6\text{H}_5$ | Nonvolatile |
| 43 | N-(12-propanoylamidododecyl)-dithiooxamide | $-(CH_2)_{12}NHC(O)CH_2CH_3$ | Nonvolatile |
| 44 | N-(12-octanoylamidododecyl)-dithiooxamide | $-(CH_2)_{12}NHC(O)(CH_2)_6CH_3$ | Nonvolatile |
| 45 | N-(2-phenylacetamidoethyl)-dithiooxamide | $-(CH_2)_2NHC(O)-CH_2-\text{C}_6\text{H}_5$ | Nonvolatile |

*Slightly Volatile

TABLE 2

Elevated Temperature Volatility of
N-Monosubstituted Dithiooxamides
$H_2NC(S)C(S)NHR$

| Ref. No. | Name of Compound | R | 49° C. | 60° C. | 71° C. |
|---|---|---|---|---|---|
| 17 | N-dodecyldithiooxamide | $-(CH_2)_{11}CH_3$ | Volatile | Volatile | Volatile |
| 21 | N-(2-octanoyloxyethyl)dithiooxamide | $-CH_2CH_2OC(O)(CH_2)_6CH_3$ | Volatile | Volatile | Volatile |
| 22 | N-(2-decanoyloxyethyl)dithiooxamide | $-CH_2CH_2OC(O)(CH_2)_8CH_3$ | Volatile | Volatile | Volatile |
| 23 | N-(2-dodecanoyloxyethyl)dithiooxamide | $-CH_2CH_2OC(O)(CH_2)_{10}CH_3$ | *Sl. Vol. | *Sl. Vol. | Volatile |
| 18 | N-tetradecyldithiooxamide | $-(CH_2)_{13}CH_3$ | **Nonvol. | *Sl. Vol. | Volatile |
| 19 | N-hexadecyldithiooxamide | $-(CH_2)_{15}CH_3$ | **Nonvol. | *Sl. Vol. | Volatile |
| 20 | N-octadecyldithiooxamide | $-(CH_2)_{17}CH_3$ | **Nonvol. | **Nonvol. | **Nonvol. |
| 25 | N-(2-octanoylamidoethyl)dithiooxamide | $-CH_2CH_2NHC(O)(CH_2)_6CH_3$ | **Nonvol. | **Nonvol. | **Nonvol. |
| 28 | N-(6-propanoylamidohexyl)dithiooxamide | $-(CH_2)_6NHC(O)CH_2CH_3$ | **Nonvol. | **Nonvol. | **Nonvol. |
| 29 | N-(6-butanoylamidohexyl)dithiooxamide | $-(CH_2)_6NHC(O)CH_2CH_2CH_3$ | **Nonvol. | **Nonvol. | **Nonvol. |
| 30 | N-(6-octanoylamidohexyl)dithiooxamide | $-(CH_2)_6NHC(O)(CH_2)_6CH_3$ | **Nonvol. | **Nonvol. | **Nonvol. |
| 31 | N-(6-undecanoylamidohexyl)dithiooxamide | $-(CH_2)_6NHC(O)(CH_2)_9CH_3$ | **Nonvol. | **Nonvol. | **Nonvol. |
| 32–33 | N-(5-propanoylamido-2-methylpentyl)-dithiooxamide mixed with N-(5-propanoylamido-4-methylpentyl)-dithiooxamide | See Table 1 for molecular formulas | **Nonvol. | **Nonvol. | **Nonvol. |
| 34–35 | N-(5-pentanoylamido-2-methylpentyl)-dithiooxamide mixed with N-(5-pentanoylamido-4-methylpentyl)-dithiooxamide | See Table 1 for molecular formulas | **Nonvol. | **Nonvol. | **Nonvol. |
| 36–37 | N-(5-heptanoylamido-2-methylpentyl)-dithiooxamide mixed with N-(5-heptanoylamido-4-methylpentyl)-dithiooxamide | See Table 1 for molecular formulas | **Nonvol. | **Nonvol. | **Nonvol. |
| 38–39 | N-(5-octanoylamido-2-methylpentyl)-dithiooxamide mixed with N-(5-octanoylamido-4-methylpentyl)-dithiooxamide | See Table 1 for molecular formulas | **Nonvol. | **Nonvol. | **Nonvol. |
| 40–41 | N-(5-nonanoylamido-2-methylpentyl)-dithiooxamide mixed with N-(5-nonanoylamido-4-methylpentyl)-dithiooxamide | See Table 1 for molecular formulas | **Nonvol. | **Nonvol. | **Nonvol. |
| 42 | N-(6-phenylacetamidohexyl)-dithiooxamide | $-(CH_2)_6NHC(O)-CH_2-\text{C}_6\text{H}_5$ | **Nonvol. | **Nonvol. | **Nonvol. |

TABLE 2-continued

Elevated Temperature Volatility of
N-Monosubstituted Dithiooxamides
$H_2NC(S)C(S)NHR$

| Ref. No | Name of Compound | R | 49° C. | 60° C. | 71° C. |
|---|---|---|---|---|---|
| 43 | N-(12-propanoylamidododecyl)-dithiooxamide | $-(CH_2)_{12}NHC(O)CH_2CH_3$ | **Nonvol. | **Nonvol. | **Nonvol. |
| 44 | N-(12-octanoylamidododecyl)-dithiooxamide | $-(CH_2)_{12}NHC(O)(CH_2)_6CH_3$ | **Nonvol. | **Nonvol. | **Nonvol. |
| 45 | N-(2-phenylacetamidoethyl)-dithiooxamide | $-(CH_2)_2NHC(O)-CH_2-\phi$ | **Nonvol. | **Nonvol. | **Nonvol. |

*Slightly Volatile
**Nonvolatile

TABLE 3

Color Coordinates of Ni(II) Complexes of
N-Monosubstituted Dithiooxamides
$H_2NC(S)C(S)NHR$

| Ref. No. | Name of Compounds | R | *Dye Concen. | Image Color | Hunter Coordinates L | n | b |
|---|---|---|---|---|---|---|---|
| 1 | N-methyldithiooxamide | $-CH_3$ | 1.0% | Blue | 39.1 | −1.6 | −16.6 |
| 2 | N-ethyldithiooxamide | $-C_2H_5$ | 1.0% | Blue | 38.5 | 2.9 | −19.3 |
| 3 | N-butyldithiooxamide | $-n-C_4H_9$ | 1.0% | Blue | 43.2 | 3.4 | −18.9 |
| 4 | N-octyldithiooxamide | $-n-C_8H_{17}$ | 1.0% | Blue | 49.4 | 1.7 | −18.3 |
| 5 | N-decyldithiooxamide | $-n-C_{10}H_{21}$ | 1.0% | Blue | 40.8 | 3.2 | −20.0 |
| 6 | N-benzyldithiooxamide | $-CH_2-C_6H_5$ | 1.0% | Blue | 41.7 | 1.2 | −20.8 |
| 7 | N-(4-chlorobenzyl)dithiooxamide | $-CH_2-C_6H_4-Cl$ | 1.0% | Blue | 49.1 | −2.2 | −17.7 |
| 8 | N-(4-methylbenzyl)dithiooxamide | $-CH_2-C_6H_4-CH_3$ | 1.0% | Blue | 44.4 | 0.3 | −20.8 |
| 9 | N-(4-dimethylaminobenzyl)dithiooxamide | $-CH_2-C_6H_4-N(CH_3)_2$ | 1.0% | Blue | 40.3 | −2.6 | −15.7 |
| 10 | N-(3,4-dichlorobenzyl)dithiooxamide | $-CH_2-C_6H_3Cl_2$ | 1.0% | Blue | 47.8 | −0.6 | −19.1 |
| 11 | N-(2-phenylethyl)dithiooxamide | $-CH_2CH_2-C_6H_5$ | 1.0% | Blue | 50.2 | 7.2 | −15.1 |
| 12 | N-(2-hydroxyethyl)dithiooxamide | $-CH_2CH_2OH$ | 1.0% | Red | 38.1 | 18.6 | −9.2 |
| 13 | N-(2-acetamidoethyl)dithiooxamide | $-CH_2CH_2NHC(O)CH_3$ | 1.0% | Blue | 47.1 | −1.7 | −18.8 |
| 14 | N-(3-diethylaminopropyl)dithiooxamide | $-CH_2CH_2CH_2N(C_2H_5)_2$ | 1.0% | Purple | 51.2 | 11.5 | −9.3 |
| 15 | N-cyclopropyldithiooxamide | cyclopropyl | 1.0% | Blue | 39.7 | 3.1 | −20.2 |

TABLE 3-continued

Color Coordinates of Ni(II) Complexes of
N-Monosubstituted Dithiooxamides
H₂NC(S)C(S)NHR

| Ref. No. | Name of Compounds | R | *Dye Concen. | Image Color | Hunter Coordinates L | a | b |
|---|---|---|---|---|---|---|---|
| 16 | N-(4-methoxybenzyl)dithiooxamide | —CH₂—⟨C₆H₄⟩—OCH₃ | 1.0% | Blue | 47.7 | −2.7 | −17.9 |
| 17 | N-dodecyldithiooxamide | —(CH₂)₁₁CH₃ | 1.0% | Blue | 47.6 | 1.9 | −20.0 |
| 18 | N-tetradecyldithiooxamide | —(CH₂)₁₃CH₃ | 2.5% | Blue | 38.7 | 4.7 | −19.1 |
| 19 | N-hexadecyldithiooxamide | —(CH₂)₁₅CH₃ | 2.5% | Blue | 43.2 | 4.8 | −10.2 |
| 20 | N-octadecyldithiooxamide | —(CH₂)₁₇CH₃ | 2.5% | Blue | 64.1 | 2.3 | −9.5 |
| 21 | N-(2-octanoyloxyethyl)dithiooxamide | —CH₂CH₂OC(O)(CH₂)₆CH₃ | 1.0% | Blue | 48.9 | −0.7 | −18.8 |
| 22 | N-(2-decanoyloxyethyl)dithiooxamide | —CH₂CH₂OC(O)(CH₂)₈CH₃ | 2.5% | Blue | 39.8 | 1.4 | −19.9 |
| 23 | N-(2-dodecanoyloxyethyl)dithiooxamide | —CH₂CH₂OC(O)(CH₂)₁₀CH₃ | 2.5% | Blue | 38.5 | 1.2 | −20.3 |
| 24 | N-(2-hexanoylamidoethyl)dithiooxamide | —CH₂CH₂NHC(O)(CH₂)₄CH₃ | 1.0% | Blue | 45.6 | −1.2 | −20.0 |
| 25 | N-(2-octanoylamidoethyl)dithiooxamide | —CH₂CH₂NHC(O)(CH₂)₆CH₃ | 2.5% | Blue | 34.1 | 2.7 | −19.2 |
| 26 | N-(1-naphthylmethyl)dithiooxamide | —CH₂—(1-naphthyl) | 1.0% | Blue | 48.2 | 0.1 | −19.2 |
| 27 | N-(11-carboxydecyl)dithiooxamide | —(CH₂)₁₀COOH | 1.0% | Blue | 50.3 | 4.6 | −18.0 |
| 28 | N-(6-propanoylamidohexyl)dithiooxamide | —(CH₂)₆NHC(O)CH₂CH₃ | 1.0% | Blue | 45.6 | 5.7 | −18.8 |
| 29 | N-(6-butanoylamidohexyl)dithiooxamide | —(CH₂)₆NHC(O)CH₂CH₂CH₃ | 1.0% | Blue | 47.8 | 3.4 | −19.0 |
| 30 | N-(6-octanoylamidohexyl)dithiooxamide | —(CH₂)₆NHC(O)(CH₂)₆CH₃ | 1.0% | Blue | 50.7 | 2.7 | −18.3 |
| 31 | N-(6-undecanoylamidohexyl)dithiooxamide | —(CH₂)₆NHC(O)(CH₂)₉CH₃ | 1.0% | Blue | 55.7 | 1.3 | −16.3 |
| 32-33 | N-(5-propanoylamido-2-methylpentyl)-dithiooxamide mixed with N-(5-propanoylamido-4-methylpentyl)-dithiooxamide | See Table 1 for molecular formulas | 1.0% | Blue | 50.3 | 1.1 | −18.8 |
| 34-35 | N-(5-pentanoylamido-2-methylpentyl)-dithiooxamide mixed with N-(5-pentanoylamido-4-methylpentyl)-dithiooxamide | See Table 1 for molecular formulas | 1.0% | Blue | 51.3 | 0.0 | −18.6 |
| 36-37 | N-(5-heptanoylamido-2-(methylpentyl)-dithiooxamide mixed with N-(5-heptanoylamido-4-methylpentyl)-dithiooxamide | See Table 1 for molecular formulas | 1.0% | Blue | 52.3 | −0.9 | −18.7 |
| 38-39 | N-(5-octanoylamido-2-methylpentyl)-dithiooxamide mixed with N-(5-octanoylamido-4-methylpentyl)-dithiooxamide | See Table 1 for molecular formulas | 1.0% | Blue | 53.0 | −0.1 | −18.1 |
| 40-41 | N-(5-nonanoylamido-2-methylpentyl)-dithiooxamide mixed with N-(5-nonanoylamido-4-methylpentyl)-dithiooxamide | See Table 1 for molecular formulas | 1.0% | Blue | 55.3 | −0.3 | −17.4 |

*Dye Concentration

TABLE 4

Color Coordinates of Ni(II) Complexes of N-Aryl Monosubstituted Dithiooxamides
H₂NC(S)C(S)NHAr**

| Ref. No. | Name of Compound | Ar | Dye Concen. | Image Color | Hunter Coordinates L | a | b |
|---|---|---|---|---|---|---|---|
| 46 | N-phenyldithiooxamide | —C₆H₅ | 1.0% | *B/G | 45.2 | −5.4 | −17.0 |
| 47 | N-(4-methylphenyl)dithiooxamide | —C₆H₄—CH₃ | 1.0% | *B/G | 46.0 | −7.3 | −17.0 |

TABLE 4-continued

Color Coordinates of Ni(II) Complexes of N-Aryl Monosubstituted Dithiooxamides
H₂NC(S)C(S)NHAr**

| Ref No. | Name of Compound | Ar | Dye Concen. | Image Color | Hunter Coordinates L | a | b |
|---|---|---|---|---|---|---|---|
| 48 | N-(4-n-butylphenyl)dithiooxamide | —⟨C₆H₄⟩—(CH₂)₃CH₃ | 1.0% | *B/G | 50.2 | −8.6 | −15.9 |
| 49 | N-(4-methoxyphenyl)dithiooxamide | —⟨C₆H₄⟩—OCH₃ | 1.0% | *B/G | 46.3 | −7.8 | −13.0 |
| 50 | N-(4-ethoxyphenyl)dithiooxamide | —⟨C₆H₄⟩—OC₂H₅ | 1.0% | *B/G | 49.9 | −9.7 | −12.9 |
| 51 | N-(4-benzyloxyphenyl)dithiooxamide | —⟨C₆H₄⟩—OCH₂(C₂H₅) | 1.0% | *B/G | 58.2 | −8.6 | −9.4 |
| 52 | N-(4-thiomethylphenyl)dithiooxamide | —⟨C₆H₄⟩—SCH₃ | 1.0% | *B/G | 51.2 | −10.4 | −8.6 |
| 53 | N-(4-chlorophenyl)dithiooxamide | —⟨C₆H₄⟩—Cl | 1.0% | *B/G | 50.2 | −5.3 | −14.0 |
| 54 | N-(4-dimethylaminophenyl)dithiooxamide | —⟨C₆H₄⟩—N(CH₃)₂ | 1.0% | *B/G | 45.2 | −6.2 | −5.3 |
| 55 | N-(4-sulfonamidophenyl)dithiooxamide | —⟨C₆H₄⟩—SO₂NH₂ | 1.0% | *B/G | 50.1 | −4.7 | −12.4 |
| 56 | N-(4-diethylaminophenyl)dithiooxamide | —⟨C₆H₄⟩—N(C₂H₅)₂ | 1.0% | *B/G | 43.8 | −5.3 | −6.1 |
| 57 | N-(2-methylphenyl)dithiooxamide | H₃C-⟨C₆H₄⟩— | 1.0% | *B/G | 42.9 | −5.5 | −21.0 |
| 58 | N-(3-trifluoromethylphenyl)dithiooxamide | —⟨C₆H₄⟩—CF₃ | 1.0% | *B/G | 54.8 | 0.5 | −9.6 |

TABLE 4-continued

Color Coordinates of Ni(II) Complexes of N-Aryl Monosubstituted Dithiooxamides
H₂NC(S)C(S)NHAr**

| Ref. No. | Name of Compound | Ar | Dye Concen. | Image Color | Hunter Coordinates | | |
|---|---|---|---|---|---|---|---|
| | | | | | L | a | b |
| 59 | N-(1-naphthyl)dithiooxamide | 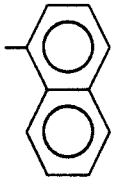 | 1.0% | *B/G | 50.8 | −9.6 | −12.0 |

*B/G — Blue-Green
**Ligands synthesized according to A. D. Grabenko et al., Zhur. Obshch. Khim. 1960, 30, 1222.

TABLE 5

Color Coordinates of Ni(II) Complexes of
N,N'-Disubstituted Dithiooxamides
RHNC(S)C(S)NHR

| Ref. No. | Name of Compound | R | *Dye Concen. | Image Color | Hunter Coordinates | | |
|---|---|---|---|---|---|---|---|
| | | | | | L | a | b |
| 60 | N,N'-di(2-octanoyloxyethyl)dithiooxamide | —CH₂CH₂OC(O)(CH₂)₆CH₃ | 1.0% | Purple | 57.4 | 15.8 | −12.2 |
| 61 | N,N'-di(2-decanoyloxyethyl)dithiooxamide | —CH₂CH₂OC(O)(CH₂)₈CH₃ | 2.5% | Purple | 41.3 | 15.6 | −17.7 |
| 62 | N,N'-di(2-dodecanoyloxyethyl)dithiooxamide | —CH₂CH₂OC(O)(CH₂)₁₀CH₃ | 2.5% | Purple | 47.4 | 12.7 | −17.0 |
| 63 | N,N'-didodecyldithiooxamide | —(CH₂)₁₁CH₃ | 1.0% | Red | 56.8 | 20.4 | −11.5 |
| 64 | N,N'-ditetradecyldithiooxamide | —(CH₂)₁₃CH₃ | 2.5% | Red | 48.4 | 28.1 | −11.0 |
| 65 | N,N'-dihexadecyldithiooxamide | —(CH₂)₁₅CH₃ | 2.5% | Red | 47.5 | 29.7 | −10.6 |
| 66 | N,N'-dioctadecyldithiooxamide | —(CH₂)₁₇CH₃ | 1.0% | Red | 71.3 | 17.6 | −2.1 |
| 67 | N,N'-dibenzyldithiooxamide | —CH₂(C₆H₅) | 1.0% | Purple | 51.1 | 16.2 | −10.5 |
| 68 | N,N'-di(6-propanoylamidohexyl)dithiooxamide | —(CH₂)₆NHC(O)CH₂CH₃ | 1.0% | Red | 61.7 | 23.4 | −3.1 |
| 69-70 | N,N'-di(5-propanoylamido-2-methylpentyl)-dithiooxamide mixed with N,N'-di(5-propanoylamido-4-methylpentyl)-dithiooxamide | See Table 1 for molecular formulas | 1.0% | Red | 64.5 | 21.5 | −4.8 |
| 71-72 | N,N'-di(5-heptanoylamido-2-methylpentyl)-dithiooxamide mixed with N,N'-di(5-heptanoylamido-4-methylpentyl)-dithiooxamide | See Table 1 for molecular formulas | 1.0% | Red | 64.6 | 15.8 | −8.6 |
| 73-74 | N,N'-di(5-octanoylamido-2-methylpentyl)-dithiooxamide mixed with N,N'-di(5-octanoylamido-4-methylpentyl)-dithiooxamide | See Table 1 for molecular formulas | 1.0% | Red | 62.5 | 18.4 | −9.1 |

*Dye Concentration

TABLE 6

Color Coordinates of Ni(II) Complexes of Mixtures of
N-(5-octanoylamido-2-methylpentyl)dithiooxamide,
N-(5-octanoylamido-4-methylpentyl)dithiooxamide,
N,N'-di(5-octanoylamido-2-methylpentyl)dithiooxamide,
and N,N'-di(5-octanoylamido-4-methylpentyl)dithiooxamide

| Ref. No. | Weight Ratio | Name of Compound** | *Dye Concen. | Image Color | Hunter Coordinates | | |
|---|---|---|---|---|---|---|---|
| | | | | | L | a | b |
| 38-39 | 100% | N-(5-octanoylamido-2-methylpentyl)-dithiooxamide mixed with N-(5-octanoylamido-4-methylpentyl)-dithiooxamide | 1.0% | Blue | 53.0 | −0.1 | −18.1 |
| 38-39 | 80% | N-(5-octanoylamido-2-methylpentyl)-dithiooxamide mixed with N-(5-octanoylamido-4-methylpentyl)-dithiooxamide mixed with | | | | | |
| 73-74 | 20% | N,N'-di(5-octanoylamido-2-methylpentyl)-dithiooxamide mixed with N,N'-di(5-octanoylamido-4-methylpentyl)-dithiooxamide | 1.0% | Blue | 54.5 | 1.6 | −17.4 |
| 38-39 | 60% | N-(5-octanoylamido-2-methylpentyl)-dithiooxamide mixed with N-(5-octanoylamido-4-methylpentyl)-dithiooxamide mixed with | | | | | |
| 73-74 | 40% | N,N'-di(5-octanoylamido-2-methylpentyl)-dithiooxamide mixed with N,N'-di(5-octanoylamido-4-methylpentyl)-dithiooxamide | 1.0% | Blue | 55.9 | 4.0 | −16.2 |
| 38-39 | 40% | N-(5-octanoylamido-2-methylpentyl)- | | | | | |

TABLE 6-continued

Color Coordinates of Ni(II) Complexes of Mixtures of
N-(5-octanoylamido-2-methylpentyl)dithiooxamide,
N-(5-octanoylamido-4-methylpentyl)dithiooxamide,
N,N'-di(5-octanoylamido-2-methylpentyl)dithiooxamide,
and N,N'-di(5-octanoylamido-4-methylpentyl)dithiooxamide

| Ref. No. | Weight Ratio | Name of Compound** | *Dye Concen. | Image Color | Hunter Coordinates L | a | b |
|---|---|---|---|---|---|---|---|
| | | dithiooxamide mixed with N-(5-octanoylamido-4-methylpentyl)-dithiooxamide mixed with | | | | | |
| 73-74 | 60% | N,N'-di(5-octanoylamido-2-methylpentyl)-dithiooxamide mixed with N,N'-di(5-octanoylamido-4-methylpentyl)-dithiooxamide | 1.0% | Blue | 55.6 | 7.7 | −16.0 |
| 38-39 | 20% | N-(5-octanoylamido-2-methylpentyl)-dithiooxamide mixed with N-(5-octanoylamido-4-methylpentyl)-dithiooxamide mixed with | | | | | |
| 73-74 | 80% | N,N'-di(5-octanoylamido-2-methylpentyl)-dithiooxamide mixed with N,N'-di(5-octanoylamido-4-methylpentyl)-dithiooxamide | 1.0% | Purple | 59.2 | 11.7 | −13.1 |
| 73-74 | 100% | N,N'-di(5-octanoylamido-2-methylpentyl)-dithiooxamide mixed with N,N'-di(5-octanoylamido-4-methylpentyl)-dithiooxamide | 1.0% | Red | 62.5 | 18.4 | −9.1 |

*Dye Concentration
**See Tables 1 and 5 for molecular formulas

What is claimed and desired to be secured by Letters Patent is as follows:

1. A construction comprising:
   (a) a first substrate with a surface on which is coated an N-(monosubstituted)dithiooxamide compound;
   (b) a second substrate with a surface on which is coated a salt of a transition metal cation with a +2 oxidation state, wherein said second substrate surface is juxtaposed in contact with said coated surface of said first substrate; and
   (c) means for separating said N-(monosubstituted)dithiooxamide from reaction with said transition metal cation until said construction is subjected to activating pressure.

2. The construction according to claim 1 wherein the N-(monosubsituted)dithiooxamide compound is a dithiooxamide compound of the formula:

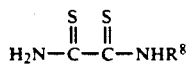

wherein $R^8$ is a suitable substituent such that the dithiooxamide compound is substantially nonvolatile at about 25° C.

3. The construction according to claim 2 wherein $R^8$ is a nonaromatic group.

4. The construction according to claim 2 wherein said surface of said first substrate, which is coated with an N-(monosubstituted)dithiooxamide, includes up to about 60 wt-% relative to total amount of mono- and di-substituted dithiooxamide, of an N,N'-(disubstituted)-dithiooxamide compound of the formula:

coated thereon.

5. The construction according to claim 1 wherein the N-(monosubstituted)dithiooxamide is an encapsulated material.

6. The construction according to claim 1 wherein said construction comprises:
   (a) a plurality of first surfaces, each of which is coated with the N-(monosubstituted)dithiooxamide;
   (b) a plurality of second surfaces, each of which is coated with the transition metal salt; and wherein
   (c) each of said coated first surfaces is juxtaposed in contact with one each of said coated second surfaces.

7. A construction comprising:
   (a) a first substrate with a surface on which is coated an N-(monosubstituted)dithiooxamide compound of the formula:

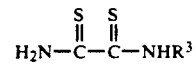

wherein $R^3$ comprises:
   (i) an alkyl or aralkyl group having 11 or more carbon atoms;
   (ii) a group of the structure $-R^4-Y-R^5$ wherein Y is a functional group selected from the group consisting of $-N(R^6)C(O)-$, $-C(O)N(R^6)-$, $-N(R^6)C(O)O-$, $-OC(O)N(R^6)-$, and $-N(R^6)C(O)N(R^7)-$, wherein $R^6$ and $R^7$ are independently hydrogen, or an alkyl or aralkyl group having 1 to 12 carbon atoms: $R^4$ is a divalent alkyl or divalent aralkyl group having 1 to 12 carbon atoms; $R^5$ is hydrogen, or an alkyl or aralkyl group having 1 to 20 carbon atoms; and, the total number of carbon atoms in $R^4$, plus $R^5$ is at least 7; or
   (iii) a group of the structure $-R^4-Y-R^5$ wherein Y is a functional group selected from the group consisting of $-OC(O)-$, $-C(O)O-$, and $-OC(O)O-$: $R^4$ is a divalent alkyl or divalent aralkyl group having 1 to 12 carbon atoms; $R^5$ is hydrogen, or an alkyl or aralkyl group having 1 to 20 carbon atoms; and, the total number of carbon atoms in $R^4$ plus $R^5$ is at least 9;

(b) a second substrate with a surface on which is coated a salt of a transition metal cation with a +2 oxidation state, wherein said surface is juxtaposed in contact with said coated surface of said first substrate; and (c) means for separating said N-(monosubstituted)dithiooxamide from reaction with said transition metal cation until said construction is subjected to activating pressure.

8. The construction according to claim 7 wherein the N-(monosubstituted)dithiooxamide is an encapsulated material.

9. The construction according to claim 7 wherein said surface of said first substrate, which is coated with an N-(monosubstituted)dithiooxamide, includes up to about 60 wt-% relative to total amount of mono- and di-substituted dithiooxamide, of an N,N'-(disubstituted)-dithiooxamide compound of the formula:

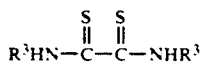

coated thereon.

10. A method of forming an image on a receptor sheet; said method comprising:

(a) providing a receptor sheet comprising a surface with a transition metal salt coated thereon; and (b) transferring to said coated surface of the receptor sheet an effective amount of an N-(monosubstituted)dithiooxamide compound.

11. The method according to claim 10 wherein said step of transferring comprises:

(a) providing a donor sheet comprising a surface with said N-(monosubstituted)dithiooxamide compound encapsulated in microcapsules and coated thereon;

(b) placing said coated surface of the donor sheet in contact with said coated surface of the receptor sheet; and (c) applying activating pressure to said donor sheet sufficient to break the microcapsules and release the encapsulated compound for transfer to said receptor sheet.

12. The method according to claim 10 wherein said N-(monosubstituted)dithiooxamide compound is represented by the formula:

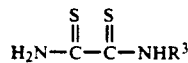

wherein $R^3$ comprises:

(a) an alkyl or aralkyl group having 11 or more carbon atoms; or (b) a group of the structure $—R^4—Y—R^5$ wherein:
(i) when Y is a functional group selected from the group consisting of $—N(R^6)C(O)—$, $—C(O)N(R^6)—$, $—N(R^6)C(O)O—$, $—OC(O)N(R^6)—$, and $—N(R^6)C(O)N(R^7)—$, wherein $R^6$ and $R^7$ are independently hydrogen, or an alkyl or aralkyl group having 1 to 12 carbon atoms; $R^4$ is a divalent alkyl or divalent aralkyl group having 1 to 12 carbon atoms; $R^5$ is hydrogen, or an alkyl or aralkyl group having 1 to 20 carbon atoms; and, the total number of carbon atoms in $R^4$ plus $R^5$ is at least 7; and (ii) when Y is a functional group selected from the group consisting of $—OC(O)—$, $—C(O)O—$, and $—OC(O)O—$: $R^4$ is a divalent alkyl or divalent aralkyl group having 1 to 12 carbon atoms; $R^5$ is hydrogen, or an alkyl or aralkyl group having 1 to 20 carbon atoms; and, the total number of carbon atoms in $R^4$ plus $R^5$ is at least 9.

13. The method according to claim 10 wherein said N-(monosubstituted)dithiooxamide compound is represented by the formula:

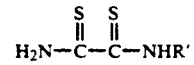

wherein R' is a suitable nonaromatic substituent such that the dithiooxamide compound is substantially nonvolatile at about 25° C.

14. The method according to claim 13 wherein R' is a group suitable such that the dithiooxamide compound is substantially nonvolatile at about 49° C.

15. The method according to claim 10 wherein said step of transferring further comprises transferring an N,N'-(disubstituted)dithiooxamide compound to the coated surface, along with the effective amount of the N-(monosubstituted)dithiooxamide compound.

16. A substrate comprising a surface on which is coated encapsulated N-(monosubstituted)dithiooxamide compound of the formula:

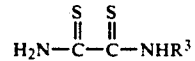

wherein $R^3$ comprises:

(a) an alkyl or aralkyl group having 11 or more carbon atoms; or (b) a group of the structure $—R^4—Y—R^5$ wherein:
(i) when Y is a functional group selected from the group consisting of $—N(R^6)C(O)—$, $—C(O)N(R^6)—$, $—N(R^6)C(O)O—$, $—OC(O)N(R^6)—$, and $—N(R^6)C(O)N(R^7)—$, wherein $R^6$ and $R^7$ are independently hydrogen, or an alkyl or aralkyl group having 1 to 12 carbon atoms; $R^4$ is a divalent alkyl or divalent aralkyl group having 1 to 12 carbon atoms; $R^5$ is hydrogen, or an alkyl or aralkyl group having 1 to 20 carbon atoms; and, the total number of carbon atoms in $R^4$ plus $R^5$ is at least 7; or (ii) when Y is a functional group selected from the group consisting of $—OC(O)—$, $—C(O)O—$, and $—OC(O)O—$: $R^4$ is a divalent alkyl or divalent aralkyl group having 1 to 12 carbon atoms; $R^5$ is hydrogen, or an alkyl or aralkyl group having 1 to 20 carbon atoms; and, the total number of carbon atoms in $R^4$ plus $R^5$ is at least 9.

17. A substrate comprising a surface on which is coated encapsulated N-(monosubstituted)dithiooxamide compound of the formula:

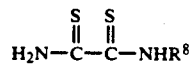

wherein $R^8$ is a suitable substituent such that the dithiooxamide compound is substantially nonvolatile at about 25° C.

18. The substrate according to claim 17 wherein $R^8$ is a nonaromatic group.

19. The substrate according to claim 17 wherein said N-(monosubstituted)dithiooxamide is encapsulated with fill solvent.

* * * * *